US008048867B2

(12) United States Patent
Nelson et al.

(10) Patent No.: US 8,048,867 B2
(45) Date of Patent: Nov. 1, 2011

(54) 9-SUBSTITUTED MINOCYCLINE COMPOUNDS

(75) Inventors: Mark L. Nelson, Norfolk, MA (US); Roger Frechette, Reading, MA (US); Peter Viski, Brookline, MA (US); Mohamed Y. Ismail, Bedford, MA (US); Todd Bowser, Charlton, MA (US); Jimmy Dumornay, Walpole, MA (US); Glen Rennie, Somerville, MA (US); Gui Liu, Medford, MA (US); Darrell J. Koza, Westerly, RI (US); Paul Sheahan, San Diego, CA (US); Karen Stapleton, Weymouth, MA (US); Paul Hawkins, Cambridge, MA (US); Beena Bhatia, Mansfield, MA (US); Atul K. Verma, Mansfield, MA (US); Laura McIntyre, Arlington, MA (US); Tadeusz Warchol, Northborough, MA (US); David Messersmith, Somerville, MA (US)

(73) Assignees: Trustees of Tufts College, Medford, MA (US); Paratek Pharmaceuticals, Inc., Boston, MA (US)

( * ) Notice: Subject to any disclaimer, the term of this patent is extended or adjusted under 35 U.S.C. 154(b) by 708 days.

(21) Appl. No.: 10/839,023

(22) Filed: May 4, 2004

(65) Prior Publication Data

US 2004/0214801 A1 Oct. 28, 2004

Related U.S. Application Data

(62) Division of application No. 09/895,857, filed on Jun. 29, 2001, now Pat. No. 6,846,939.

(60) Provisional application No. 60/216,659, filed on Jul. 7, 2000, provisional application No. 60/275,621, filed on Mar. 13, 2001.

(51) Int. Cl.
*A61K 31/59* (2006.01)
*C07C 401/00* (2006.01)

(52) U.S. Cl. ........................................ 514/152; 552/203

(58) Field of Classification Search .................. 552/205, 552/203; 514/152
See application file for complete search history.

(56) References Cited

U.S. PATENT DOCUMENTS

| | | | |
|---|---|---|---|
| 2,980,584 A | 4/1961 | Hammer | |
| 2,990,331 A | 6/1961 | Neumann et al. | |
| 3,007,965 A | 11/1961 | Growich, Jr. et al. | |
| 3,062,717 A | 11/1962 | Hammer | |
| 3,165,531 A | 1/1965 | Blackwood et al. | |
| 3,219,671 A | 11/1965 | Hlavka, et al. | |
| 3,226,436 A | 12/1965 | James et al. | |
| RE26,253 E | 8/1967 | Petisi et al. | |
| 3,338,963 A | 8/1967 | James et al. | |
| RE26,271 E | 9/1967 | Boothe et al. | |
| 3,341,585 A | 9/1967 | Martell, Jr. et al. | |
| 3,345,410 A | 10/1967 | Winterbottom et al. | |
| 3,360,561 A | 12/1967 | Zambrano | |
| 3,373,193 A | 3/1968 | Schroeder et al. | |
| 3,397,230 A | 8/1968 | Winterbottom et al. | |
| 3,454,697 A | 7/1969 | Hoyner, et al. | |
| 3,483,251 A | 12/1969 | Zambrano | |
| 3,518,306 A | 6/1970 | Ross, et al. | |
| 3,557,280 A | 1/1971 | Weber et al. | |
| 3,579,579 A | 5/1971 | Ross et al. | |
| 3,674,859 A | 7/1972 | Beutel et al. | |
| 3,901,942 A | 8/1975 | Bernardi et al. | |
| 3,957,980 A | 5/1976 | Noseworthy | |
| 4,018,889 A | 4/1977 | Armstrong | |
| 4,024,272 A | 5/1977 | Rogalski et al. | |
| 4,126,680 A | 11/1978 | Armstrong | |
| 5,021,407 A | 6/1991 | Levy | |
| 5,248,797 A | 9/1993 | Sum | |
| 5,258,372 A | 11/1993 | Levy | |
| 5,281,628 A | 1/1994 | Hlavka et al. | |
| 5,284,963 A | 2/1994 | Sum et al. | |
| 5,326,759 A | 7/1994 | Hlavka et al. | |
| 5,328,902 A | 7/1994 | Sum et al. | |
| 5,371,076 A | 12/1994 | Lee et al. | |
| 5,380,888 A | 1/1995 | Sum et al. | |
| 5,386,041 A | 1/1995 | Sum et al. | |
| 5,401,729 A | 3/1995 | Sum et al. | |
| 5,401,863 A | 3/1995 | Hlavka et al. | |
| 5,420,272 A | 5/1995 | Sum et al. | |
| 5,430,162 A | 7/1995 | Sum et al. | |
| 5,442,059 A | 8/1995 | Sum et al. | |
| 5,457,096 A | 10/1995 | Sum et al. | |
| 5,466,684 A | 11/1995 | Sum et al. | |
| 5,494,903 A | 2/1996 | Hlavka et al. | |

(Continued)

FOREIGN PATENT DOCUMENTS

EP 0 535 346 B1 4/1993

(Continued)

OTHER PUBLICATIONS

Barden, Timothy, et al., "'Glycylcyclines'. 3. 9-Aminodoxycyclinecarboxamides," *J. Med. Chem.*, vol. 37:3205-3211 (1994).

Koza, Darrell J., et al., "Synthesis and Biological Evaluation of 9-Substituted Tetracycline Derivatives," *Bioorganic & Medicinal Chemistry Letters*, vol. 12:2163-2165 (2002).

Peterson, P.J., et al., "In Vitro and In Vivo Antibacterial Activities of a Novel Glycylcycline, the 9-*t*-Butylglycylamido Derivative of Minocycline (GAR-936)," *Antimicrobial Agents and Chemotherapy*, vol. 43(4):738-744 (1999).

(Continued)

*Primary Examiner* — Sabiha Qazi
(74) *Attorney, Agent, or Firm* — Mintz Levin Cohn Ferris Glovsky and Popeo, P.C.; Ivor R. Elrifi; Heidi A. Erlacher

(57) ABSTRACT

The present invention pertains, at least in part, to novel 9-substituted minocycline compounds. These minocycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

42 Claims, No Drawings

U.S. PATENT DOCUMENTS

| | | | |
|---|---|---|---|
| 5,495,018 A | 2/1996 | Sum et al. |
| 5,495,030 A | 2/1996 | Sum et al. |
| 5,495,031 A | 2/1996 | Sum et al. |
| 5,512,553 A | 4/1996 | Sum et al. |
| 5,529,990 A | 6/1996 | Hlavka et al. |
| 5,530,117 A | 6/1996 | Hlavka et al. |
| 5,532,227 A | 7/1996 | Golub et al. |
| 5,567,692 A | 10/1996 | Sum et al. |
| 5,639,742 A | 6/1997 | Lee et al. |
| 5,675,030 A | 10/1997 | Krishnan et al. |
| 5,789,395 A | 8/1998 | Amin et al. |
| 5,834,450 A | 11/1998 | Su |
| 5,886,175 A | 3/1999 | Sum et al. |
| 6,500,812 B2 | 12/2002 | Nelson et al. |
| 6,506,740 B1 | 1/2003 | Ashley et al. |
| 6,617,318 B1 | 9/2003 | Nelson et al. |
| 6,624,168 B2 | 9/2003 | Nelson et al. |
| 6,642,270 B2 | 11/2003 | Nelson et al. |
| 6,683,068 B2 | 1/2004 | Nelson et al. |
| 6,818,634 B2 | 11/2004 | Nelson et al. |
| 6,818,635 B2 | 11/2004 | Nelson et al. |
| 6,833,365 B2 | 12/2004 | Levy et al. |
| 6,841,546 B2 | 1/2005 | Draper et al. |
| 6,846,939 B2 | 1/2005 | Nelson et al. |
| 6,849,615 B2 | 2/2005 | Nelson et al. |
| 7,001,918 B2 | 2/2006 | Huss et al. |
| 7,045,507 B2 | 5/2006 | Draper et al. |
| 7,056,902 B2 | 6/2006 | Nelson et al. |
| 7,067,681 B2 | 6/2006 | Nelson et al. |
| 7,094,806 B2 | 8/2006 | Nelson |
| 7,202,035 B2 | 4/2007 | Squires et al. |
| 2002/0103171 A1 | 8/2002 | Nelson et al. |
| 2002/0111335 A1 | 8/2002 | Nelson et al. |
| 2002/0115644 A1 | 8/2002 | Levy et al. |
| 2002/0128237 A1 | 9/2002 | Nelson et al. |
| 2002/0193354 A1 | 12/2002 | Nelson et al. |
| 2003/0100017 A1 | 5/2003 | Draper et al. |
| 2003/0125348 A1 | 7/2003 | Nelson et al. |
| 2003/0166585 A1 | 9/2003 | Draper et al. |
| 2004/0033996 A1 | 2/2004 | Nelson et al. |
| 2004/0063674 A1 | 4/2004 | Levy et al. |
| 2004/0092490 A1 | 5/2004 | Draper et al. |
| 2004/0138183 A1 | 7/2004 | Nelson et al. |
| 2004/0176334 A1 | 9/2004 | Nelson et al. |
| 2004/0192657 A1 | 9/2004 | Garcia-Luzon et al. |
| 2004/0214800 A1 | 10/2004 | Levy et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0250744 A1 | 11/2005 | Levy et al. |
| 2005/0288262 A1 | 12/2005 | Bandarage et al. |
| 2006/0003971 A1 | 1/2006 | Nelson |
| 2006/0084961 A1 | 4/2006 | Huss et al. |
| 2006/0089336 A1 | 4/2006 | Nelson et al. |
| 2006/0148765 A1 | 7/2006 | Nelson |
| 2006/0166944 A1 | 7/2006 | Berniac |
| 2006/0166945 A1 | 7/2006 | Abato |
| 2006/0166946 A1 | 7/2006 | Nelson et al. |
| 2006/0194773 A1 | 8/2006 | Levy |
| 2006/0205698 A1 | 9/2006 | Nelson et al. |
| 2007/0167415 A1 | 7/2007 | Levy et al. |

FOREIGN PATENT DOCUMENTS

| | | |
|---|---|---|
| EP | 0 536 515 B1 | 4/1993 |
| EP | 0536515 B1 | 4/1993 |
| EP | 0 582 788 B1 | 2/1994 |
| EP | 0 582 789 B1 | 2/1994 |
| EP | 0 582 790 B1 | 2/1994 |
| EP | 0 582 810 B1 | 2/1994 |
| EP | 0 582 829 | 2/1994 |
| EP | 0 618 190 | 10/1994 |
| FR | 302929 | 12/1964 |
| FR | 2208885 | 6/1974 |
| GB | 921252 | 3/1963 |
| GB | 955766 | 4/1964 |
| GB | 1469384 | 4/1977 |
| WO | WO-96/34852 A1 | 11/1996 |
| WO | WO-00/28983 A1 | 5/2000 |
| WO | WO 01/19784 A1 | 3/2001 |
| WO | WO 01/74761 A1 | 10/2001 |
| WO | WO-02/04406 A2 | 1/2002 |

OTHER PUBLICATIONS

Spencer, John L., et al., "6-Deoxytetracyclines. V.$^{1a}$ 7,9-Disubstituted Products," *J. Med. Chem.*, vol. 122:405-407 (1963).

Sum, Phaik-Eng, et al., "Synthesis and Structure—Activity Relationship of Novel Glycylcycline Derivatives Leading to the Discovery of GAR-936," *Bioorganic & Medicinal Chemistry Letters*, vol. 9:1459-1462 (1999).

Sum, P.E., et al., "Recent developments in tetracycline antibiotics," *Curr. Pharm. Des.*, vol. 4(2):119-132 (1998).

Tally, F.T., et al., "Glycylcyclines: a new generation of tetracyclines," *Journal of Antimicrobial Chemotherapy*, vol. 35:449-452 (1995).

Baldini, M., et al. "Diazo derivatives of amino acids and peptides as possible antineoplastic chemotherapeutic agents. 1. General considerations and methods." *Boll Soc Ital Biol Sper.* Jun. 30, 1960; 36:577-81.

Barden, T.C., et al. ""Glycylcyclines". 3. 9-Aminodoxycyclinecarboxamides."*J Med Chem.* Sep. 30, 1994; 37(20):3205-11.

Berge, S.M. et al. (Jan. 1977) "Pharmaceutical Salts", *J. Pharm. Sci* 66(1):1-19.

Boothe, J., et al. "6-Deoxytetracyclines. I. Chemical modification by electrohilic substitution." *J. Am. Chem. Soc.* Mar. 5, 1960; 82:1253-4.

Borowski, E., et al. "Perimycin, Type of Heptaene Antifungal Antibiotic." CA56:14402i.

Branceni, D., et al. "Use of tetracycline for the demonstration of the phenomena of extra-osseous calcification." *C.R. Seances Soc Biol Fil.* 1961; 155:1469-72.

Dumova, A.M. "Effect of tetracycline and oxytetracycline on the adrenal function." *Antibiotiki.* Jul. 1965; 10(7):647-50.

Eidus, L., et al. "Comparative Expts. On the Tetracycline Analogs." CA56:16090c.

*Federal Register.* 1962; 27:3851.

Garrod, L.P. "Recent developments in antibiotic therapy." *Recenti Prog Med.* Jan. 1962; 32:3-24.

Genazzini, E., et al. *Atti. Soc. Ital. Sci. Vet.* 1964; 18:175-8.

Good, W. "The inhibition of haemolysis by phloridzin." *Biochim Biophys Acta.* Jan. 29, 1962; 56:359-61.

Hajdu, P. *Arzneimittel-Forsch.* 1962; 12:206-7.

Maniar, A., et al. "One of the factors influencing the action of antibiotics." *Ann Inst Pasteur* (Paris). Dec. 1961; 101:887-97.

Martell, et al. *J. Med. Chem.* 1967; 10(3);359-63.

Ritzerfeld, W., et al. "In vitro studies on 2 old and 2 new tetracycline preparations." *Arzneimittelforschung.* Jan. 1962; 12:30-2.

Strel'nokov. Effect of Tetracyclines on the Heart in Experiments by the Data of Electrocardiograms. *Antibiotiki.* 1965; 10(7):650-6.

Sum, P., et al. "Glycylcyclines. 1. A new generation of potent antibacterial agents through modification of 9-aminotetracyclines." *J Med Chem.* Jan. 7, 1994; 37(1):184-8.

Van den Bogert, C., et al. "Doxycycline in combination chemotherapy of a rat leukemia." *Cancer Res.* Dec. 1, 1988; 48(23):6686-90.

European Search Report for Application No. 06007501.7-2103, dated Jun. 6, 2006.

Orth, Peter et al., "Crystal Structure of the tet Repressor in Complex with Novel Tetracycline, 9-(N, N-dimethylglycylamido)-6-demethyl-6-deoxy-tetracycline", J. Mol. Biol., vol. 285, pp. 455-561 (1999).

Testa, Raymond T. et al., "In Vitro and in Vivo Antibacterial Activities of the Glycylcyclines, a New Class of Semisynthetic Tetracyclines", Antimicrob. Agents Chemother., vol. 37, pp. 2270-2277 (1993).

Goldstein, F.W. et al., "N, N-Dimethylglycyl-Amido Derivative of Minocycline and 6-Demythyl-6-Desoxytetracycline, Two New Glycylcyclines Highly Effective against Tetracycline-Resistant Gram-Positive Cocci", Antimicrob. Agents Chemother., vol. 38, pp. 2218-2220 (1994).

Johnson, D.M. et al. "Two Investigational Glycylcyclines, DMG-DMDOT and DMG-MINO Antimicrobial Activity Studied Against Gram-Positive Species", Diagn. Microbiol. Infect. Dis., vol. 24, pp. 53-57 (1996).

Petersen, P.J. et al. "In Vitro and in Vivo Antibacterial Activities of a Novel Glycylcycline, the 9-t-Butylglycylamido Derivative of Minocycline (GAR-936)", Antimicrob. Agents Chemother., vol. 43, pp. 738-744 (1999).

9-SUBSTITUTED MINOCYCLINE COMPOUNDS

RELATED APPLICATIONS

This application is a division of U.S. patent application Ser. No. 09/895,857, entitled "9-Substituted Minocycline Compounds," filed on Jun. 29, 2001, which claims priority to U.S. Provisional Patent Application Ser. No. 60/275,621, entitled "9-Substituted Minocycline Compounds," filed on Mar. 13, 2001, and U.S. Provisional Patent Application Ser. No. 60/216,659, entitled "9-Substituted Minocycline Compounds," filed on Jul. 7, 2000. This application is related to U.S. Provisional Application Nos. 60/154,701, filed on Sep. 14, 1999; 60/193,972, filed on Mar. 31, 2000; 60/193,879, filed on Mar. 31, 2000; 60/204,158, filed on May 15, 2000; 60/212,030, filed Jun. 16, 2000; and 60/212,471, filed Jun. 16, 2000. The entire contents of each of the aforementioned applications are hereby incorporated herein by reference in their entirety.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972. Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice.

SUMMARY OF THE INVENTION

The invention pertains, at least in part, to minocycline compounds of formula I:

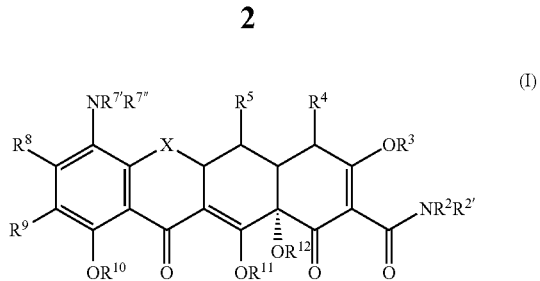

wherein:
X is $CHC(R^3Y'Y)$, $CR^{6'}R^6$, S, $NR^6$, or O;
$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, aryl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;
Z is $CR^{9d}R^{9e}$, S, $NR^{9b}$ or O;
Z' is $NR^{9f}$, O or S;
$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The invention also pertains, at least in part, to 9-substituted minocycline compounds of the formula (II):

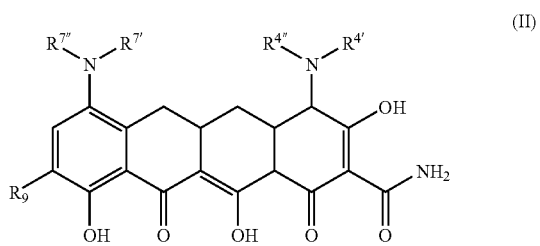

wherein:
$R^{4'}$, $R^{4''}$, $R^{7'}$ and $R^{7''}$ are each alkyl; and

R⁹ is a pyridylethynyl group; an alkenylcarbamate group; a halo group; an alkylacrylate group; a naphthyl group; a haloacetyl group; an alkyl carbamate group; a cyclopentyl or cyclopentenyl group; a benzofuranyl group; a phenylpropiononeamino group; a tosylamino group; a methoxypyridyl group; an alkeneamino group; an N-t-butyl group; a t-butylamide group; a hydroxybutylamino group; a hydroxypropylamino group; a phenyl group; a nitrophenyl group; a nitrophenyl alkynyl group; an aminophenyl group; an alkoxyphenyl group; a halophenyl urea group; a cyanophenyl group; a carboxyphenyl group; an acylphenyl group; an alkylphenyl group; a halophenyl group; an alkoxyphenyl group; a carboxyalkylphenyl group; a phenylalkynyl group; an alkynyl group; an alkylglycineethylester group; a styrene group; a thiophene group; and an alkylarninophospho group; and pharmaceutically acceptable salts, esters and prodrugs thereof.

The invention also pertains to methods of using the minocycline compounds of the invention to treat subjects suffering from states which can treated using the minocycline compounds of the invention.

The invention also pertains to pharmaceutical compositions comprising the minocycline compounds of the invention and a pharmaceutically acceptable carrier. The invention also pertains to the use of a minocycline compound of the invention for the manufacture of a medicament, e.g., a medicament for the treatment of a tetracycline responsive state.

DETAILED DESCRIPTION OF THE INVENTION

The present invention pertains, at least in part, to novel 9-substituted minocycline compounds. These minocycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The invention pertains, at least in part, to minocycline compounds of Formula I:

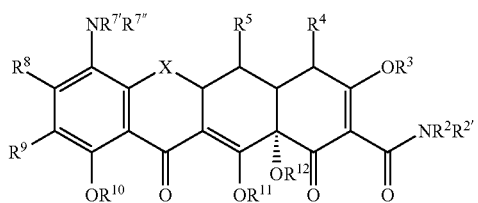

wherein:
X is $CHC(R^{13}Y'Y)$, $CR^{6'}R^6$, S, $NR^6$, or O;
$R^2$, $R^{4'}$, $R^{4''}$, $R^{7'}$ and $R^{7''}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^4$ is $NR^{4'}R^{4''}$, alkyl, alkenyl, alkynyl, aryl, hydroxyl, halogen, or hydrogen;
$R^{2'}$, $R^3$, $R^{10}$, $R^{11}$ and $R^{12}$ are each hydrogen or a pro-drug moiety;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
$R^9$ is nitro, alkyl, alkenyl, alkynyl, aryl, alkoxy, alkylthio, alkylsulfinyl, alkylsulfonyl, arylalkyl, amino, arylalkenyl, arylalkynyl, thionitroso, or $-(CH_2)_{0-3}NR^{9c}C(=Z')ZR^{9a}$;
Z is $CR^{9d}R^{9e}$, S, $NR^{9b}$ or O;
Z' is $NR^{9f}$, O or S;
$R^{9a}$, $R^{9b}$, $R^{9c}$, $R^{9d}$, $R^{9e}$ and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or an arylalkyl;
$R^{13}$ is hydrogen, hydroxy, alkyl, alkenyl, alkynyl, alkoxy, alkylthio, alkylsulfinyl, alkylsulfonyl, alkylamino, or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl, and pharmaceutically acceptable salts, esters and prodrugs thereof.

The term minocycline compounds refers to compounds of formula (I) above. In an embodiment, the term minocycline compounds include compounds wherein X is $CR^6R^{6'}$; $R^2$, $R^{2'}$, $R^5$, $R^6$, $R^{6'}$, $R^8$, $R^9$, $R^{10}$, $R^{11}$, and $R^{12}$ are each hydrogen; $R^4$ is $NR^{4'}R^{4''}$; and $R^{4'}$, and $R^{4''}$, $R^{7'}$, and $R^{7''}$ are each lower alkyl, e.g., methyl.

Examples of $R^9$ include substituted and unsubstituted aryl groups. The aryl groups include substituted and unsubstituted heteroaryls (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, oxazolyl, isooxazolyl, naphthridinyl, thiazolyl, isothiazolyl, or deazapurinyl), substituted or unsubstituted phenyl, and groups with more than one aromatic ring, such as naphthyl.

Examples of substituents of $R^9$ include, but are not limited to, alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the aryl $R^9$ group is substituted with one or more substituents such as, for example, carboxylate, alkyl, alkenyl, alkynyl, aryl, heterocyclic, cyano, amino, halogen, alkoxy, alkoxycarbonyl, amido, alkylcarbonyl, or nitro.

In another embodiment, $R^9$ is substituted or unsubstituted alkynyl. The alkynyl $R^9$ group may be substituted with a substituted or unsubstituted aryl group, such as, for example, phenyl. The possible substituents for the substituted phenyl group include, for example, those listed supra, for the aryl $R^9$ group. Furthermore, the substituted alkynyl $R^9$ group may be substituted with a heteroaryl (e.g., pyridinyl), alkyl (e.g., methyl, ethyl, propyl, butyl, pentyl, hexyl, cyclopropyl, cyclobutyl, cyclopentyl, cyclohexyl, etc.), alkenyl (e.g., ethenyl, propenyl, butenyl, pentenyl, hexenyl, etc.), carboxylate, silyl (e.g., trialkylsilyl, e.g., trimethylsilyl), aralkyl, or a alkyloxycarbonyl group.

Each of these groups may also be further substituted, with such substituents as alkyl, alkenyl, halogen, hydroxyl, alkoxy, alkylcarbonyloxy, alkyloxycarbonyl, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In a further embodiment, the alkynyl $R^9$ group is substituted with an aminoalkyl group. The aminoalkyl group may then also be substituted with, for example, an alkyl, alkenyl, alkynyl, acyl, carbonyl, or alkylsulfone group.

In another further embodiment, the alkynyl $R^9$ group is substituted with a cycloalkenyl group, such as, for example, cyclopentene.

In another embodiment, $R^9$ is alkyl. The alkyl group may be substituted or unsubstituted. Examples of alkyl groups include, for example, both straight chain, branched and cyclic alkyl groups. For example, alkyl groups include methyl, ethyl, i-propyl, n-propyl, i-butyl, n-butyl, t-butyl, pentyl, hexyl, heptyl, octyl, nonyl, decyl, etc. Cyclic alkyl groups include groups with one or more rings, such as, for example, cyclopropane, cyclobutane, cyclopentane, cyclohexane, cycloheptane, etc. In an embodiment, the alkyl $R^9$ group is 2-cyclopentylethyl.

Examples of substituents of alkyl groups include, for example, halogens (e.g., fluorine, chlorine, bromine, iodine, etc.), hydroxyl, alkoxy (e.g., methoxy, ethoxy, propoxy, butoxy, pentoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, carboxy, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amido, imino, sulfhydryl, alkylthio, arylthio, thiocarboxylate, sulfate, alkylsulfinyl, alkenyl, sulfonato, sulfamoyl, sulfonamido, nitro, alkenyl, cyano, azido, heterocyclyl, alkylaryl, aryl and heteroaryl.

In another embodiment, the minocycline compound of the invention is a compound wherein $R^9$ is —NR$^{9c}$C(=Z')ZR$^{9a}$, —CH$_2$NR$^{9c}$C(=Z')ZR$^{9a}$, —(CH$_2$)$_2$NR$^{9c}$C(=Z')ZR$^{9a}$, or —(CH$_2$)$_3$NR$^{9c}$C(=Z')ZR$^{9a}$. In certain embodiments, $R^9$ is —NR$^{9c}$C(=Z')ZR$^{9a}$ or —CH$_2$NR$^{9c}$C(=Z')ZR$^{9a}$. Examples of $R^{9c}$ include hydrogen. Z' may be, for example, S, NH, or O. Examples of Z include NR$^{9b}$ (e.g., when $R^{9b}$ is hydrogen, alkyl, etc.), O or S.

Examples of $R^{9a}$ groups include aryl groups such as substituted and unsubstituted phenyl. Examples of possible substituents of aryl $R^{9a}$ groups include, but are not limited to, alkyl (e.g., methyl, ethyl, propyl, butyl, pentyl, hexyl, perfluormethyl, perchloroethyl, etc.), alkenyl, halogen (e.g., fluorine, chlorine, bromine, iodine, etc.), hydroxyl, alkoxy (e.g., methoxy, ethoxy, propoxy, perfluoromethoxy, perchloromethoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylarnino, amido, imino, sulfhydryl, alkylthio, arylthio, thiocarboxylate, sulfate, alkylsulfinyl, sulfonato, sulfamoyl, sulfonamido, nitro, acetyl, alkyl, cyano, azido, heterocyclyl, alkylaryl, aryl and heteroaryl groups.

In certain embodiments, at least one of the substituents of the substituted phenyl is nitro, alkoxy (e.g., methoxy, methylenedioxy, perfluoromethoxy) alkyl (e.g., methyl, ethyl, propyl, butyl, or pentyl), acetyl, halogen (e.g., fluorine, chlorine, bromine, or iodine), or amino (e.g., dialkylamino). In certain embodiments, the alkoxy group is perhalogenated, e.g., perfluoromethoxy.

Examples of aryl $R^{9a}$ groups include, but are not limited to, unsubstituted phenyl, para-nitrophenyl, para-methoxy phenyl, para-perfluoromethoxy phenyl, para-acetyl phenyl, 3,5-methylenedioxyphenyl, 3,5-diperfluoromethyl phenyl, para-bromo phenyl, para-chloro phenyl, and para-fluoro phenyl.

Other examples of aryl $R^{9a}$ groups include substituted and unsubstituted heterocycles (e.g., furanyl, imidazolyl, benzothiophenyl, benzofuranyl, quinolinyl, isoquinolinyl, benzodioxazolyl, benzoxazolyl, benzothiazolyl, benzoimidazolyl, methylenedioxyphenyl, indolyl, thienyl, pyrimidyl, pyrazinyl, purinyl, pyrazolyl, pyrolidinyl, oxazolyl, isooxazolyl, naphthridinyl, thiazolyl, isothiazolyl, or deazapurinyl) and substituted and unsubstituted biaryl groups, such as naphthyl and fluorene.

$R^{9a}$ also may be substituted or unsubstituted alkyl, e.g., methyl, ethyl, propyl, butyl, pentyl, etc. Examples of substituents include but are not limited to halogens (e.g., fluorine, bromine, chlorine, iodine, etc.), hydroxyl, alkoxy (e.g., methoxy, ethoxy, propoxy, butoxy, etc.), alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, silyl, aminocarbonyl, alkylthiocarbonyl, phosphate, phosphonato, phosphinato, cyano, amino, acylamino, amidino, imino, sulflhydryl, alkylthio, arylthio, thiocarboxylate, sulfate, alkylsulfinyl, sulfonato, sulfamoyl, sulfonamido, nitro, trifluoromethyl, cyano, azido, alkenyl, heterocyclyl, alkylaryl, aryl and heteroaryl.

$R^{9a}$ also can be substituted or unsubstituted alkenyl. Examples of substituents for alkenyl $R^{9a}$ groups include those listed above for alkyl $R^{9a}$ groups. Examples of alkenyl $R^9$ groups include pent-1-enyl.

In an embodiment, Z' is NH, Z is NH, and $R^{9a}$ is alkyl.

The invention also pertains to compounds wherein $R^9$ is aminoalkyl (e.g., aminomethyl). Aminoalkyl $R^9$ groups may be further substituted. Examples of substituents include aryl groups, such as, for example substituted or unsubstituted phenyl (e.g., methylenedioxyphenyl or para-perfluoromethoxyphenyl), or heteroaromatic groups which allows the compound of the invention to perform its intended function.

Examples of minocycline compounds of the invention include those listed in Table 1, as well as the ones listed below:

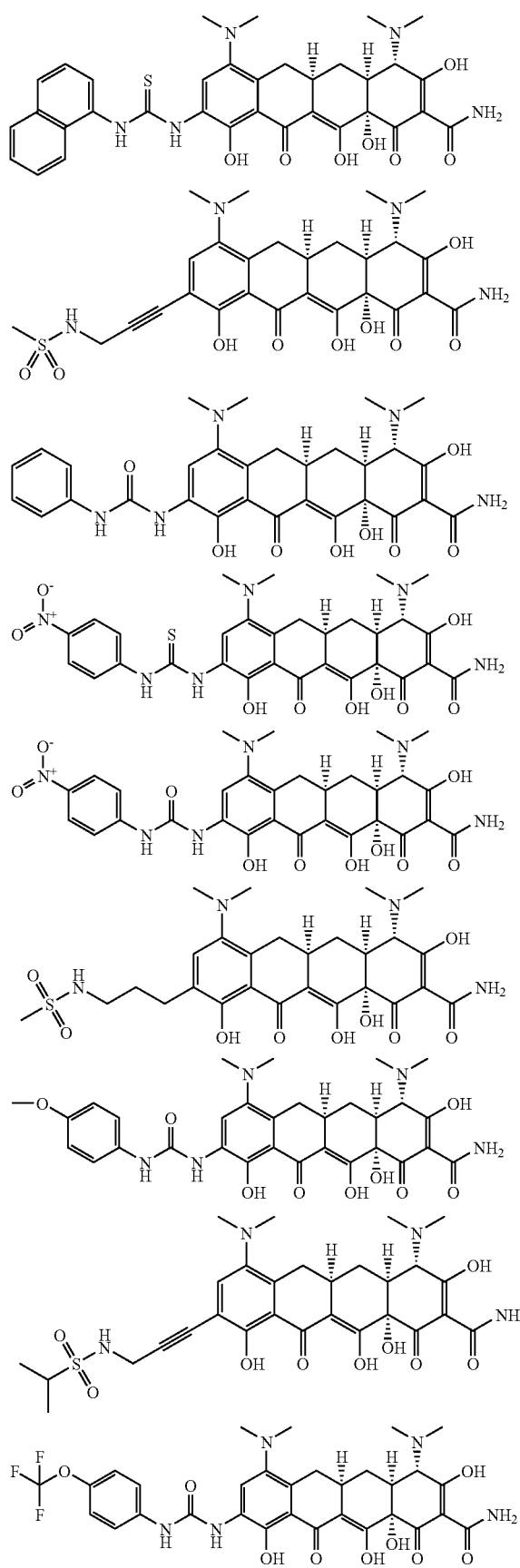
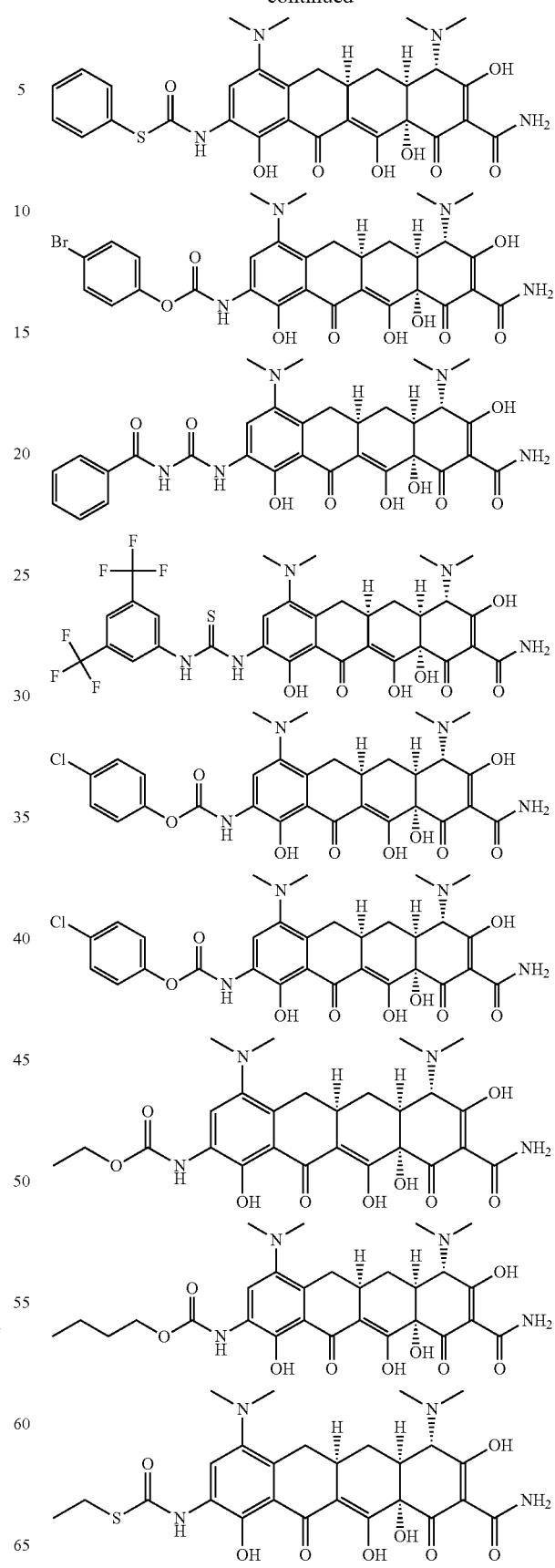

9
-continued
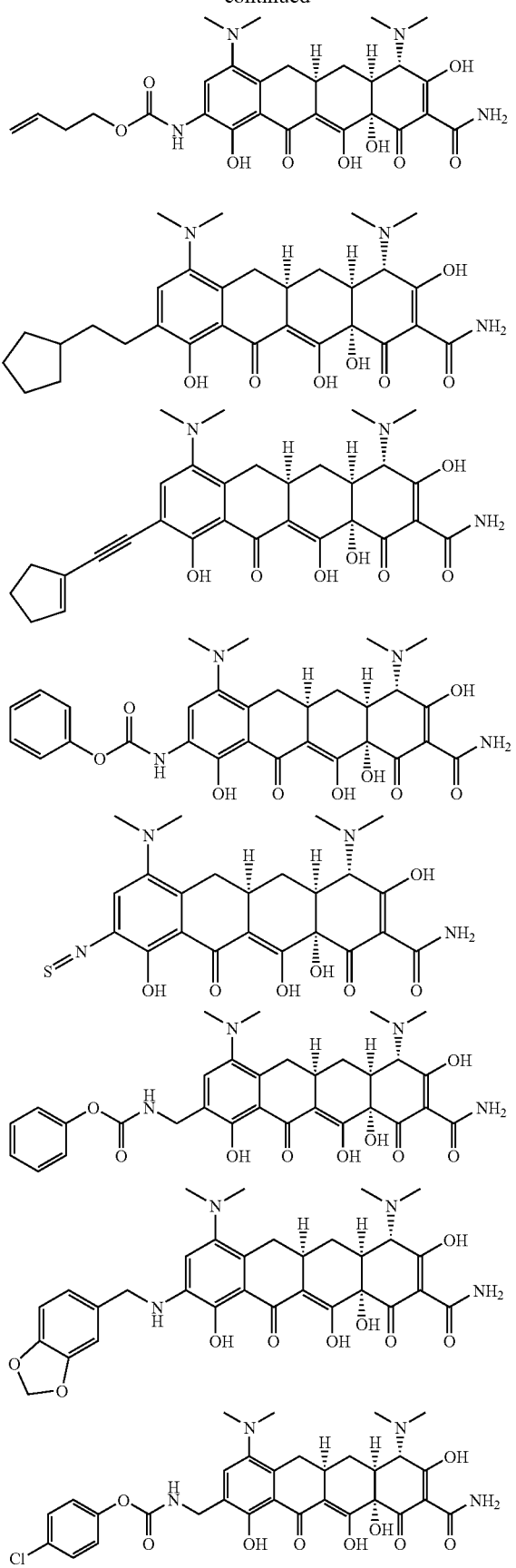
10
-continued
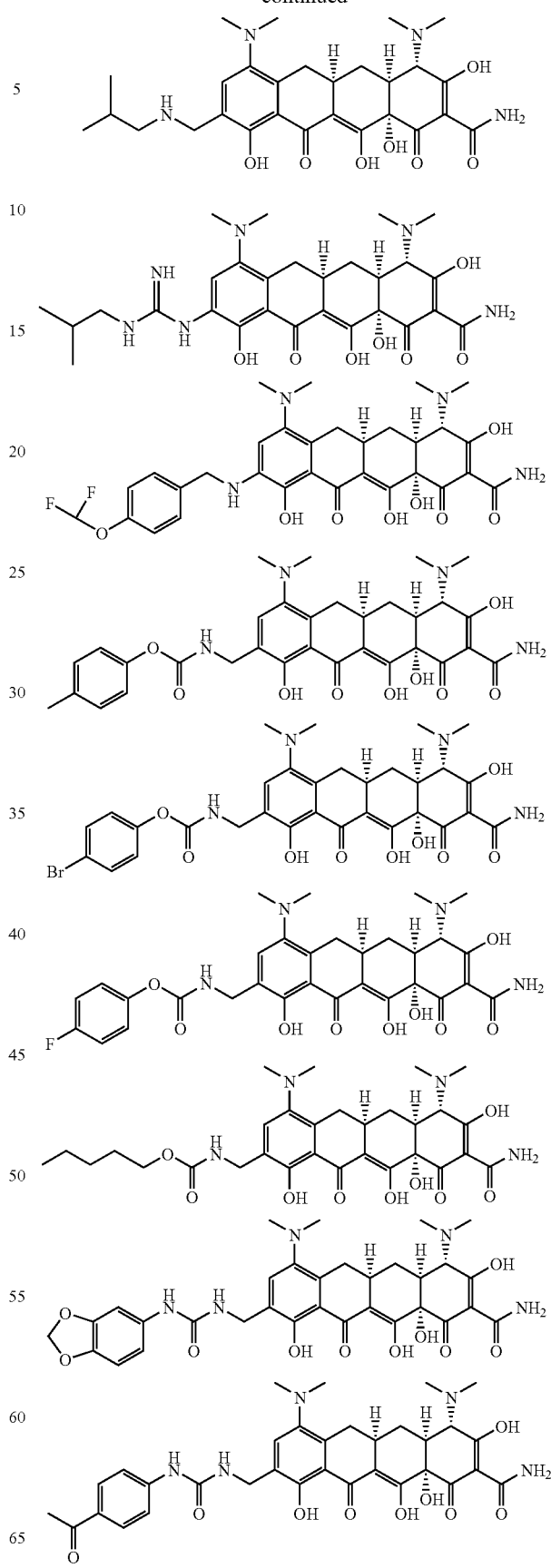

-continued

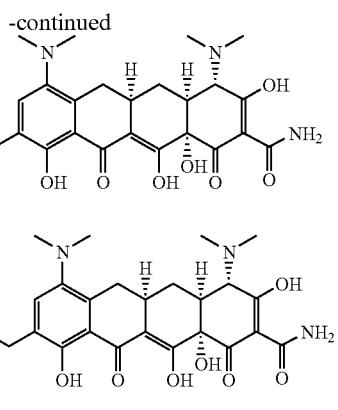

Pharmaceutically acceptable salts of these compounds are also included. Other compound of the invention are listed in Table 1.

The invention also relates, at least in part, to 9-substituted minocycline compounds of the formula:

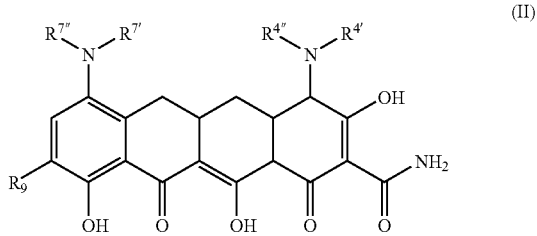

(II)

wherein:
$R^{4'}$, $R^{4''}$, $R^{7'}$, and $R^{7''}$ are each alkyl; and
$R^9$ is a pyridylethynyl group; an alkenylcarbamate group; a halo group; an alkylacrylate group; a naphthyl urea group; a haloacetyl group; an alkyl carbamate group; a cyclopentyl or cyclopentenyl group; a benzofuranyl group; a phenylpropiononeamino group; a tosylamino group; a methoxypyridyl group; an alkeneamino group; an N-t-butyl group; a t-butylamide group; a hydroxybutylamino group; a hydroxypropylamino group; a phenyl group; a nitrophenyl group; a nitrophenyl alkynyl group; an aminophenyl group; a halophenyl urea group; an alkoxyphenyl group; a cyanophenyl group; a carboxyphenyl group; an acylphenyl group; an alkylphenyl group; a halophenyl group; an alkoxyphenyl group; a carboxyalkylphenyl group; a phenylalkynyl group; an alkynyl group; an alkylglycineethylester group; a styrene group; a thiophene group; an alkylaminophospho group; and pharmaceutically acceptable salts thereof.

The term "9-substituted minocycline compound" includes minocycline compounds with a substituent at the 9 position. In another embodiment, the compound is a derivative of minocycline.

In an embodiment, $R^9$ is an alkenylcarbamate group. Examples of tetracycline compounds with this $R^9$ substituent include 9-isopropenyl carbamate minocycline.

In an embodiment, $R^9$ is a pyridylethynyl group. Examples of tetracycline compounds with this $R^9$ substituent include 9-(2-pyridylethynyl) minocycline.

In an embodiment, $R^9$ is a halo group. Examples of tetracycline compounds with this $R^9$ substituent include 9-iodo minocycline.

In an embodiment, $R^9$ is an alkylacrylate group. Examples of tetracycline compounds with this $R^9$ substituent include 9-butylacrylate minocycline.

In an embodiment, $R^9$ is a naphthyl urea group. Examples of tetracycline compounds with this $R^9$ substituent include 9-naphthyl minocycline urea.

In an embodiment, $R^9$ is a haloacetyl group. Examples of tetracycline compounds with this $R^9$ substituent include 9-chloroacetyl minocycline urea.

In an embodiment, $R^9$ is an alkyl carbamate group. Examples of tetracycline compounds with this $R^9$ substituent include 9-neopentyl minocycline carbamate.

In an embodiment, $R^9$ is a cyclopentyl or cyclopentenyl group. Examples of tetracycline compounds with this $R^9$ substituent include 9-cyclopentene minocycline.

In an embodiment, $R^9$ is a benzofuranyl group. Examples of tetracycline compounds with this $R^5$ substituent include 9-benzofuranyl minocycline.

In an embodiment, $R^9$ is a phenylpropiononeamino group. Examples of tetracycline compounds with this $R^9$ substituent include 9-(phenylpropiononeamino) minocycline.

In an embodiment, $R^9$ is a tosylamino group. Examples of tetracycline compounds with this $R^9$ substituent include 9-tosylamino minocycline.

In an embodiment, $R^9$ is a methoxypyridyl group. Examples of tetracycline compounds with this $R^5$ substituent include 9-(2-methoxy-3-pyridyl) minocycline.

In an embodiment, $R^5$ is an alkeneamino group. Examples of tetracycline compounds with this $R^9$ substituent include 9-(N-2'-hydroxydecyl-9'-ene-amino) minocycline.

In an embodiment, $R^9$ is an N-t-butyl group. Examples of tetracycline compounds with this $R^9$ substituent include N-t-butyl-minocycline HCl.

In an embodiment, $R^9$ is a t-butylamide group. Examples of tetracycline compounds with this $R^9$ substituent include 9-BOC—NH minocycline.

In an embodiment, $R^9$ is a hydroxybutylamino group. Examples of tetracycline compounds with this $R^9$ substituent include 9-(N-2'-hydroxybutylamino) minocycline.

In an embodiment, $R^9$ is a hydroxypropylamino group. Examples of tetracycline compounds with this $R^9$ substituent include 9-(N-3-chloro, 2-hydroxylpropylamino) minocycline.

In an embodiment, $R^9$ is a phenyl group. Examples of tetracycline compounds with this $R^9$ substituent include 9-phenyl minocycline HCl and 9-p-tolyl minocycline.

In an embodiment, $R^9$ is a nitrophenyl group. Examples of tetracycline compounds with this $R^9$ substituent include 9-(3'-nitrophenyl) minocycline.

In an embodiment, $R^9$ is a nitrophenyl alkynyl group. Examples of tetracycline compounds with this $R^9$ substituent include 9-(4'-nitrophenylethynyl) minocycline.

In an embodiment, $R^9$ is an aminophenyl group. Examples of tetracycline compounds with this $R^9$ substituent include 9-(3-aminophenyl) minocycline.

In an embodiment, $R^9$ is a halophenyl urea group; Examples of tetracycline compounds with this $R^9$ substituent include 9-(4-chloro,2-trifluoromethylphenyl) minocycline urea.

In an embodiment, $R^9$ is an alkoxyphenyl group. Examples of tetracycline compounds with this $R^9$ substituent include 9-(p-methoxyphenyl) minocycline, 9-(4'-methoxyphenyl) minocycline, and 9-(3,4-methylenedioxyphenyl) minocycline.

In an embodiment, $R^9$ is a cyanophenyl group. Examples of tetracycline compounds with this $R^9$ substituent include 9-(4'-cyanophenyl) minocycline.

In an embodiment, $R^9$ is a carboxyalkylphenyl group. Examples of tetracycline compounds with this $R^9$ substituent include 9-(4'-carboxyphenyl) minocycline.

In an embodiment, R⁹ is an acylphenyl group. Examples of tetracycline compounds with this R⁹ substituent include 9-(3-formylphenyl) minocycline.

In an embodiment, R⁹ is an alkylphenyl group. Examples of tetracycline compounds with this R⁹ substituent include 9-(4'-t-butylphenyl) minocycline.

In an embodiment, R⁹ is a halophenyl group. Examples of tetracycline compounds with this R⁹ substituent include 9-(3-chlorophenyl) minocycline, 9-(2',4'-difluorophenyl) minocycline, 9-(3,4-difluorophenyl) minocycline, 9-(4'-chlorophenyl) minocycline, 9-(3,4-dichlorophenyl) minocycline, and 9-(4'-trifluoromethylphenyl) minocycline.

In an embodiment, R⁹ is an alkoxyphenyl group. Examples of tetracycline compounds with this R⁹ substituent include 9-(3-ethoxyphenyl) minocycline.

In an embodiment, R⁹ is a carboxyalkylphenyl group. Examples of tetracycline compounds with this R⁹ substituent include 9-(4-carboxymethylphenyl) minocycline.

In an embodiment, R⁹ is a phenylalkynyl group. Examples of tetracycline compounds with this R⁹ substituent include 9-(phenylethynyl) minocycline, 9-(3-hydroxyphenylethynyl) minocycline, 9-(p-tolylethynyl) minocycline, and 9-(p-methoxyphenylethynyl) minocycline.

In an embodiment, R⁹ is an alkynyl group. Examples of tetracycline compounds with this R⁹ substituent include 9-ethynyl minocycline, 9-(p-fluoroethynyl) minocycline, 9-(trimethylsilylethynyl) minocycline, 9-(propionyl) minocycline, 9-(cyclohexenylethynyl) minocycline, and 9-(1-cyclohexyl-1-hydroxyethynyl) minocycline.

In an embodiment, R⁹ is an alkylglycineethylester group. Examples of tetracycline compounds with this R⁹ substituent include 9-propylglycineethylester minocycline HCl, and 9-methylglycineethylester minocycline.

In an embodiment, R⁹ is a styrene group. Examples of tetracycline compounds with this R⁹ substituent include 9-(styrene) minocycline, 9-(4'-fluorostyrene) minocycline.

In an embodiment, R⁹ is a thiophene group. Examples of tetracycline compounds with this R⁹ substituent include 9-(2-thiophene) minocycline, and 9-(5'-chloro-2'-thiophene) minocycline.

In an embodiment, R⁹ is an alkylaminophospho group. Examples of tetracycline compounds with this R⁹ substituent include 9-(p-methoxyphenylaminophospho) minocycline, and 9-(phenylaminophospho) minocycline.

The minocycline compounds of this invention can be synthesized using the methods described in Schemes 1-6.

9-substituted minocyclines can be synthesized by the following general method, shown in Scheme 1.

SCHEME 1

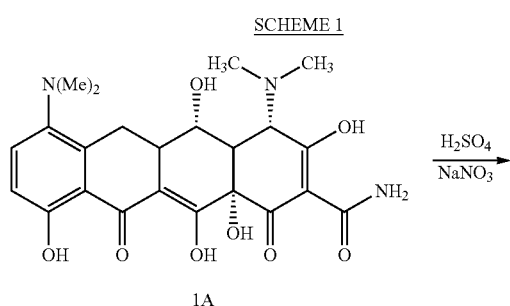

1A

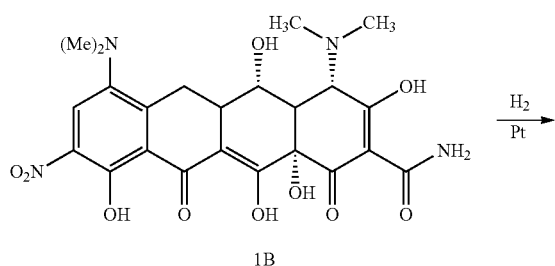

1B

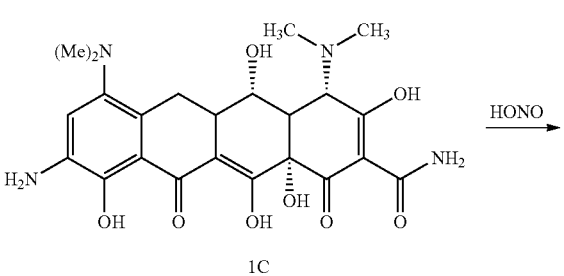

1C

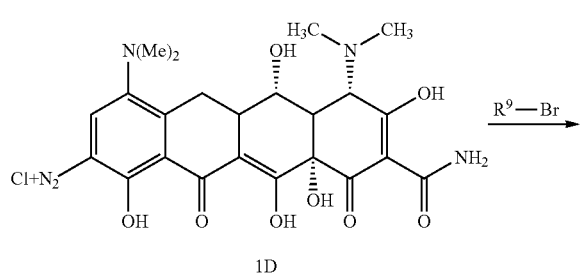

1D

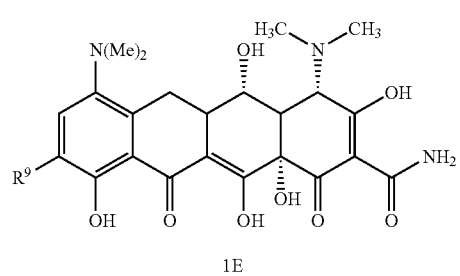

1E

Generally, 9-substituted minocycline compounds can be synthesized as shown in Scheme 2 by treating minocycline (1A), with sulfuric acid and sodium nitrate. The resulting product is 9-nitro (1B) minocycline. The nitro minocycline compound is then treated with hydrogen gas and a platinum catalyst to yield the 9-amino minocycline compound, 1C. To synthesize 9 derivatives, the 9-amino minocycline compound is treated with HONO, to yield the diazonium salt (1D). The salt can subsequently be treated with numerous compounds possessing an alkene or π bond functional group such as alkenes, aryls, and alkynyls (e.g., R⁹Br) yielding the 9-substituted minocycline compound (1E).

SCHEME 2

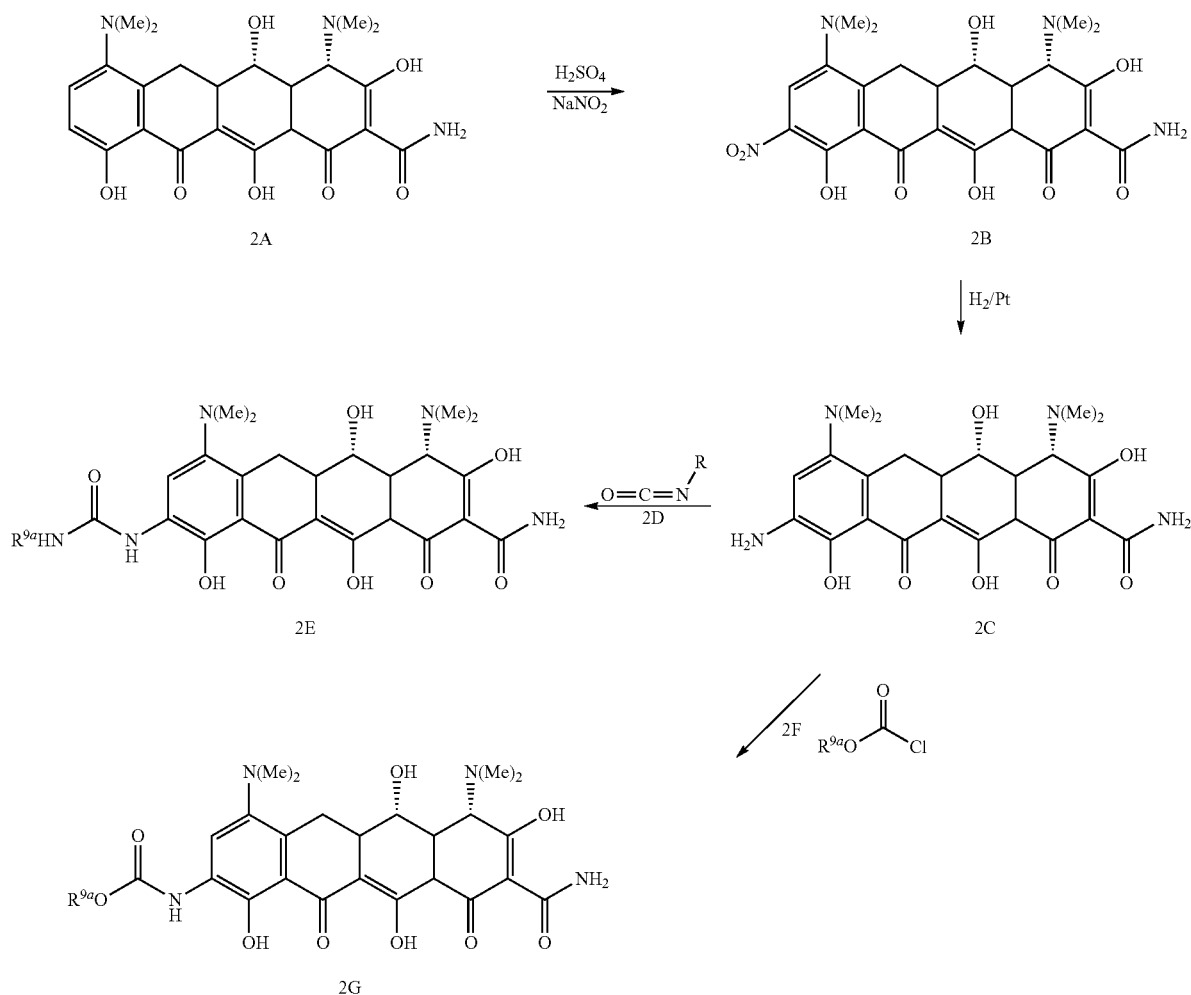

As shown in Scheme 3, minocycline compounds of the invention wherein $R^9$ is a carbamate or a urea derivative can be synthesized using the following protocol. Minocycline (2A) is treated with $NaNO_2$ under acidic conditions forming 9-nitro minocycline (2B). 9-nitrominocycline (2B) is then treated with $H_2$ gas and a platinum catalyst to form the 9-amino minocycline derivative (2C). To form the urea derivative (2E), isocyanate (2D) is reacted with the 9-amino minocycline derivative (2C). To form the carbamate (2G), the appropriate acid chloride ester (2F) is reacted with 2C.

SCHEME 3

-continued

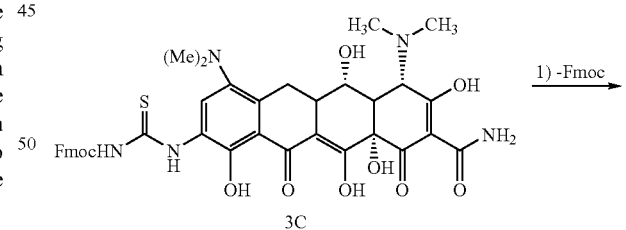

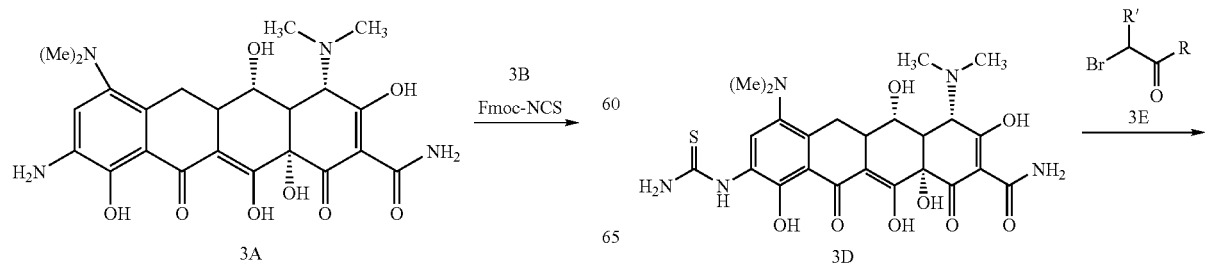

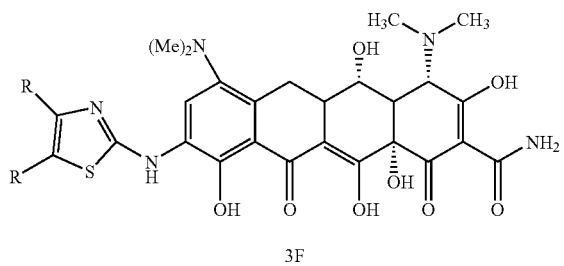

3F

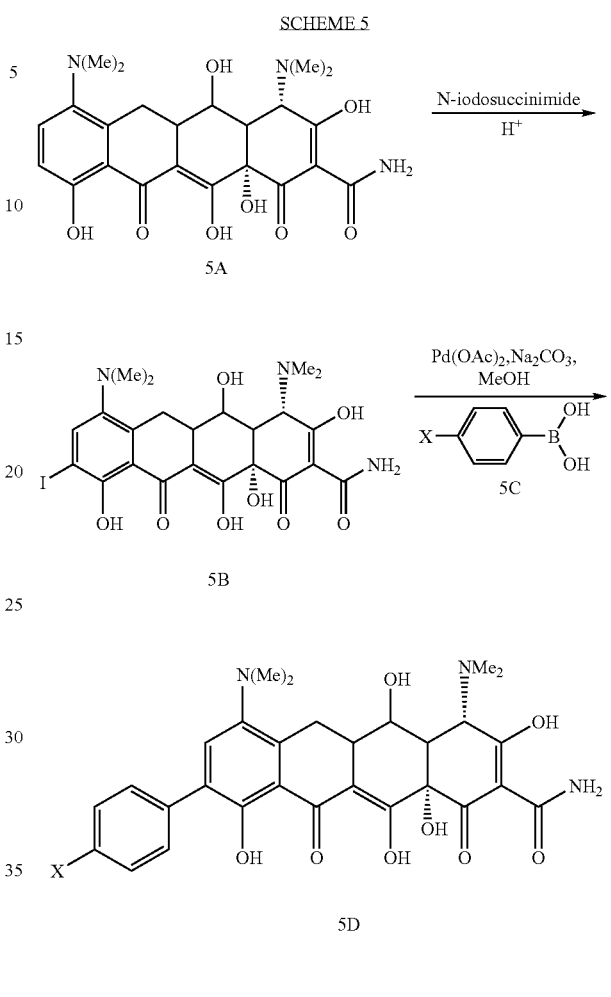

As shown in Scheme 3, minocycline compounds of the invention, wherein $R^9$ is a heterocyclic (i.e. thiazole) substituted amino group can be synthesized using the above protocol. 9-amino minocycline (3A) is reacted with Fmoc-isothiocyanate (3B) to produce the protected thiourea (3C). The protected thiourea (3C) is then deprotected yielding the active tetracycline urea or tetracycline thiourea (3D) compound. The tetracycline thiourea (3D) is reacted with an α-haloketone (3E) to produce a thiazole substituted 9-amino minocycline (3F).

SCHEME 4

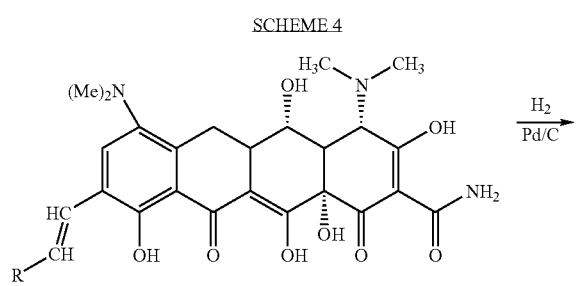

As shown in Scheme 4, 9-alkenyl minocycline compounds (4A) can be hydrogenated to form alkyl 9-substituted minocycline compounds (4B). Scheme 4 depicts the selective hydrogenation of the 9-position double bond, with hydrogen gas and a palladium/carbon catalyst. Similarly, 9-alkynyl minocyclines also can be hydrogenated to form 9-alkyl minocycline compounds.

In Scheme 5, a general synthetic scheme for synthesizing 9-position aryl derivatives of a minocycline compound is shown. In Scheme 5, a Suzuki coupling of an aryl boronic acid with an iodomrinocycline compound is shown. An iodo minocycline compound (5B) can be synthesized from sancycline by treating minocycline (5A) with at least one equivalent N-iodosuccinimide (NIS) under acidic conditions. The reaction is quenched, and the resulting 9-iodo minocycline (5B) can then be purified using standard techniques known in the art. To form the aryl derivative, 9-iodo minocycline (5B) is treated with boronic acid (5C) plus aqueous sodium carbonate, and is catalyzed with palladium. The product (5D) can be purified by methods known in the art (such as HPLC). Other 9-aryl minocycline compounds can be synthesized using similar protocols.

The 9-substituted minocycline compounds of the invention can also be synthesized using Stille cross couplings. Stille cross couplings can be performed using an appropriate tin reagent (e.g., R—SnBu$_3$) and a halogenated tetracycline compound, (e.g., 9-iodominocycline). The tin reagent and the iodominocycline compound can be treated with a palladium catalyst (e.g., Pd(PPh$_3$)$_2$Cl$_2$ or Pd(AsPh$_3$)$_2$Cl$_2$) and, optionally, with an additional copper salt, e.g., CuI. The resulting compound can then be purified using techniques known in the art.

SCHEME 6

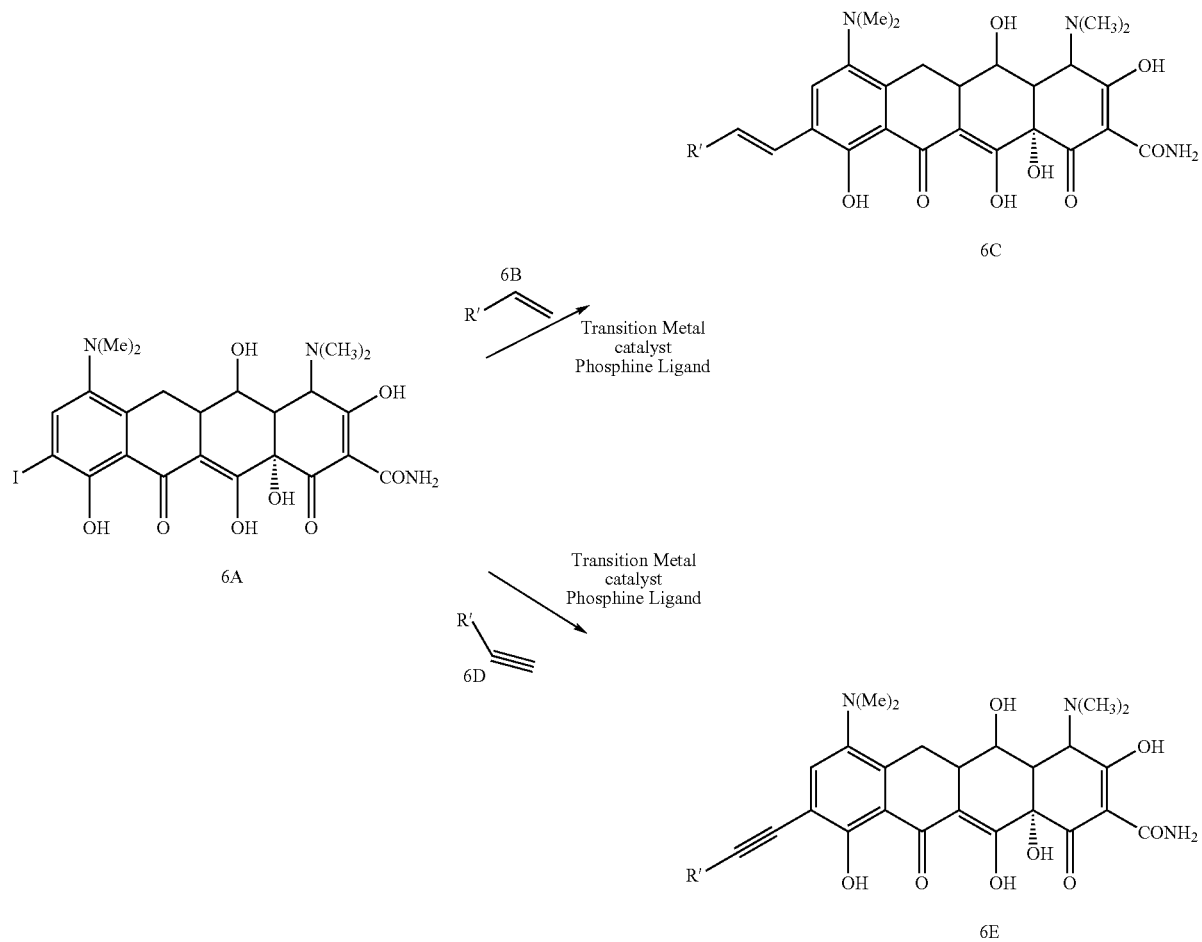

The compounds of the invention can also be synthesized using Heck-type cross coupling reactions. As shown in Scheme 6, Heck-type cross-couplings can be performed using a halogenated tetracycline compound (e.g., 9-iodominocycline, 6A), a reactive alkene (6B) or alkyne (6D), and an appropriate palladium or other transition metal catalyst. The resulting 9-substituted alkenyl (6C) or 9-substituted alkynyl (6E) minocycline compound can then be purified using techniques known in the art.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuiran, purine, benzofiran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylarnino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkyls, and alkthioalkynyls. The term "alkthioalkyls" include compounds with an alkyl, alkenyl, or alkynyl group bonded to a sulfur atom which is bonded to an alkyl group. Similarly, the term "alkthioalkyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^{31}$.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the minocycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

The invention also pertains to methods for treating a tetracycline responsive states in subjects, by administering to a subject an effective amount of a minocycline compound of the invention (e.g., a compound of Formula (I), (II) or shown in Table 1), such that the tetracycline responsive state is treated.

The language "tetracycline compound responsive state" includes states which can be treated, prevented, or otherwise ameliorated by the administration of a minocycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.*, 48:6686-6690 (1988)). For certain tetracycline responsive state, a minocycline compound of the invention with little or no antibacterial activity may be desirable.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commission for Clinical Laboratory Standards*, Document M7-A2, vol. 10, no. 8, pp. 13-20, $2^{nd}$ edition, Villanova, Pa. (1990).

The minocycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the minocycline compound is used to treat a bacterial infection that is resistant to other tetracycline antibiotic compounds. The minocycline compound of the invention may be administered with a pharmaceutically acceptable carrier.

The language "effective amount" of the compound is that amount necessary or sufficient to treat or prevent a tetracycline compound responsive state. The effective amount can vary depending on such factors as the size and weight of the subject, the type of illness, or the particular minocycline compound. For example, the choice of the minocycline compound can affect what constitutes an "effective amount". One of ordinary skill in the art would be able to study the aforementioned factors and make the determination regarding the effective amount of the minocycline compound without undue experimentation.

The invention also pertains to methods of treatment against microorganism infections and associated diseases. The methods include administration of an effective amount of one or more minocycline compounds to a subject. The subject can be either a plant or, advantageously, an animal, e.g., a mammal, e.g., a human.

In the therapeutic methods of the invention, one or more minocycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

The invention also pertains to pharmaceutical compositions comprising a therapeutically effective amount of a minocycline compound and, optionally, a pharmaceutically acceptable carrier.

The language "pharmaceutically acceptable carrier" includes substances capable of being coadministered with the minocycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The minocycline compounds of the invention that are basic in nature are capable of forming a wide variety of salts with various inorganic and organic acids. The acids that may be used to prepare pharmaceutically acceptable acid addition salts of the minocycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a minocycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other minocycline compounds of the invention not specifically described in the foregoing experimental section can be accomplished using combinations of the reactions described above that will be apparent to those skilled in the art.

The preparation of other minocycline compounds of the invention not specifically described in the foregoing experimental section can be accomplished using combinations of the reactions described above that will be apparent to those skilled in the art.

The minocycline compounds of the invention that are acidic in nature are capable of forming a wide variety of base salts. The chemical bases that may be used as reagents to prepare pharmaceutically acceptable base salts of those minocycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of minocycline compounds of the invention that are acidic in nature may be formed with pharmaceutically acceptable cations by conventional methods. Thus, these salts may be readily prepared by treating the minocycline compound of the invention with an aqueous solution of the desired pharmaceutically acceptable cation and evaporating the resulting solution to dryness, preferably under reduced pressure. Alternatively, a lower alkyl alcohol solution of the minocycline compound of the invention may be mixed with an alkoxide of the desired metal and the solution subsequently evaporated to dryness.

The preparation of other minocycline compounds of the invention not specifically described in the foregoing experimental section can be accomplished using combinations of the reactions described above that will be apparent to those skilled in the art.

The minocycline compounds of the invention and pharmaceutically acceptable salts thereof can be administered via either the oral, parenteral or topical routes. In general, these compounds are most desirably administered in effective dosages, depending upon the weight and condition of the subject-being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The minocycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium. stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior minocycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of minocyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

In one embodiment, the minocycline compounds of the invention do not include those described in U.S. patent application Ser. No. 09/823,884, incorporated herein by reference.

Furthermore, the invention also pertains to the use of a minocycline compound of formula I or II, for the preparation of a medicament. The medicament may include a pharmaceutically acceptable carrier and the minocycline compound is an effective amount, e.g., an effective amount to treat a tetracycline responsive state.

EXEMPLIFICATION OF THE INVENTION

Compounds of the invention may be made as described below, with modifications to the procedure below within the skill of those of ordinary skill in the art.

Example 1

Preparation of Minocycline Compounds of the Invention

Preparation of 9-Iodominocycline

To 200 ml of 97% methanesulfonic acid was slowly added, at ambient temperature, portionwise [30 g; 56.56 mM] of minocycline-bis-hydrochloride salt. The dark yellow brown solution was then stirred at ambient temperature while [38 g; 169.7 mM] of N-iodosuccinimide was added, in six equal portions, over 3.0 hours time. The reaction was monitored via analytical LC, noting the disappearance of the starting material.

The reaction was slowly quenched into 2 L of ice cold water containing [17.88 g; 1134.1 mM] of sodium thiosulfate with rapid stirring. This quench was stirred for approximately 30 minutes at ambient temperature. The aqueous layer was then extracted with 6×200 ml of ethyl acetate before the aqueous was poured onto [259.8 g; 3.08M] of sodium hydrogen carbonate containing 300 ml of n-butanol. The phases were split and the aqueous extracted with 4×250 ml of n-butanol. The organic fractions were combined and washed with 3×250 ml of water and once with 250 ml of saturated brine. The resulting organic phase was reduced to dryness under reduced pressure. The residue was suspended in methanol (~600 ml) and anhydrous HCl gas was bubbled into this mixture until solution occurred This solution was reduced to dryness under reduced pressure. The filtrates were reduced to dryness under reduced pressure. The resulting material was triturated with 300 ml of methyl t-butyl ether and isolated via filtration. This material was redissolved in 300 ml of methanol and treated with 0.5 g of wood carbon, filtered and filtrates reduced to dryness under reduced pressure. The material was again powdered under methyl t-butyl ether, isolated via suction filtration and washed with more ether, and finally hexanes. The material was vacuum dried to give 22.6 g of a light yellow brown powder.

General Procedure for Preparation of 9-Alkynyl Minocycline Compounds 1 mmol 9-iodo minocycline, 50 mg tetrakis tripenylphosphinato palladate, 12 mg palladium acetate, 32 mg copper (I) iodide are dissolved/suspended in 10 ml acetonitrile. 2 to 5 ml triethylamine and 3 to 5 mmol alkynyl derivative is added. The reaction mixture is vigorously stirred between ambient temperature to 70° C. The reaction time is 2-24 hours. When the reaction is completed the dark suspension is filtered through a celite bed and concentrated. The crude product is purified by prep HPLC. The combined fractions are concentrated and taken up in ~1 ml methanol. ~3 ml HCl saturated methanol is added, and the product is precipitated with ether.

General Procedure for Preparation of 9-Aryl Minocycline Compounds 0.15 mmol of 9-iodominocycline, PdOAc (3.2 mg), 229 μl 2M $Na_2CO_3$ and 2 equivalents of phenyl boronic acid were dissolved/suspended in 10 ml methanol. The reaction flask was purged with argon and the reaction run for a minimum of four hours or until HPLC monitoring shows consumption of starting material and/or the appearance of products. The suspension was filtered through celite, and subject to purification by prep HPLC on a divinylbenzene column.

Compound OU (9-(4-Trifluoromethoxyphenylureido)-Methyl Minocycline)

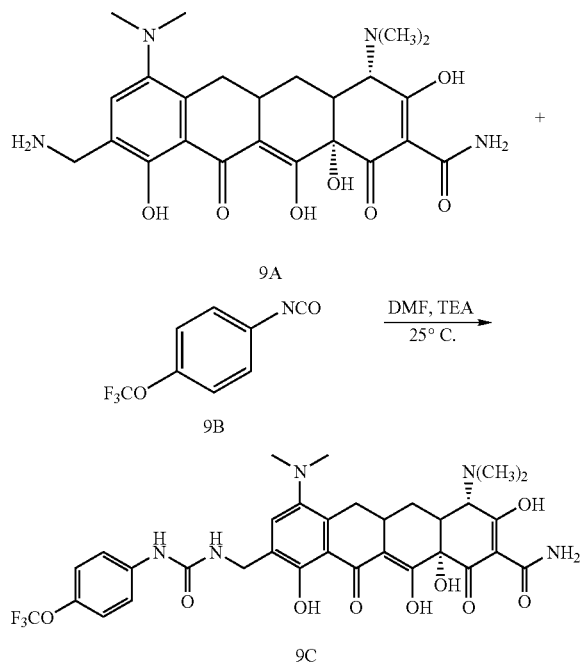

To 3 mL of dimethylformamide was added 150 mg (0.25 mmol) of 9-methyl aminominocyline trihydrochloride and 67 mL (0.50 mmol) of triethylamine at 25° C. With stirring, 75 mL (0.50 mmol) of 4-trifluoromethoxyphenylisocyanate was added and the resulting reaction mixture was stirred at 25° C. for two hours. The reaction was monitored by analytical HPLC (4.6×50 mm reversed phase Luna C18 column, 5 minute linear gradient 1-100% B buffer, A buffer was water with 0.1% trifluoroacetic acid, B buffer was acetonitrile with 0.1% trifluoroacetic acid). Upon completion, the reaction was quenched with 1 mL of water and the pH adjusted to approximately 2.0 with concentrated HCl. The solution was filtered and the compound purified by preparative HPLC. The yield of compound OU was 64 mg (37% yield). The purity of Compound OU was 95% determined by LCMS (M+1=690).

Compound LA (9-(4'Carboxy phenyl) Minocycline)

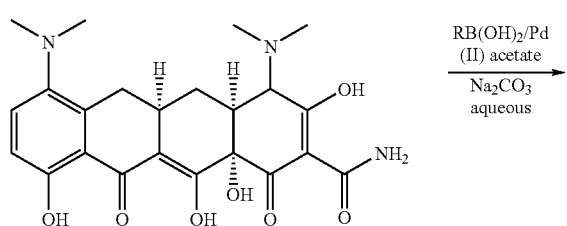

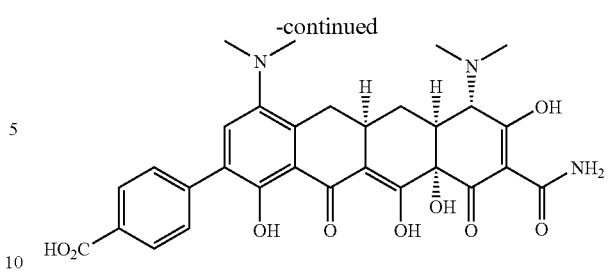

In a clean, dry reaction vessel, was placed 9-iodominocycline [500 mg; 0.762 mmoles] bis HCl salt, palladium (II) acetate [17.2 mg; 0.076 mmoles] along with 10 ml of reagent grade methanol. The solution was immediately purged, with stirring, with a stream of argon gas for approximately 5 minutes. The reaction vessel was brought to reflux and to it was sequentially added via syringe 2M potassium carbonate solution [1.91 ml; 3.81 mmoles], followed by a solution of p-carboxyphenyl boronic acid [238.3 mg; 1.53 mmoles] in 5 ml of reagent DMF. Both of these solutions were previously degassed with argon gas for approximately 5 minutes. The reaction was heated for 45 minutes, the progress was monitored via reverse phase HPLC. The reaction was suctioned filtered through a pad of diatomaceous earth and washed the pad with DMF. The filtrates were reduced to an oil under vacuum and residue treated with t-butylmethyl ether. Crude material was purified via reverse phase HPLC on DVB utilizing a gradient of water and methanol/acetonitrile containing 1.0% trifluoroacetic acid. Product confirmed by mass spectrum: found M+1 578.58; the structure corroborated with 1H NMR.

Example 2

In Vitro Minimum Inhibitory Concentration (MIC) Assay

The following assay is used to determine the efficacy of minocycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The minocycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1\times10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions are added to each well of microtiter plates. The final cell density should be approximately $5\times10^5$ CFU/ml. These plates are incubated at 35° C. in an ambient air incubator for approximately 18 hr. The plates are read with a microplate reader and are visually inspected when necessary. The MIC is defined as the lowest concentration of the minocycline compound that inhibits growth. Compounds of the invention indicate good inhibition of growth.

In Table 1, compounds which were good inhibitors of growth of a particular bacteria are indicated with *, compounds which were very good inhibitors of a particular bacteria are indicated with , and compounds with were particularly good inhibitors of a particular bacteria are indicated with *.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

TABLE 1

| ID | STRUCTURE | S. aureus | E. hirae | E. coli |
|---|---|---|---|---|
| KA | 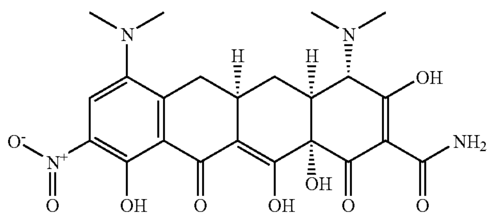 |  |  | * |
| KB | 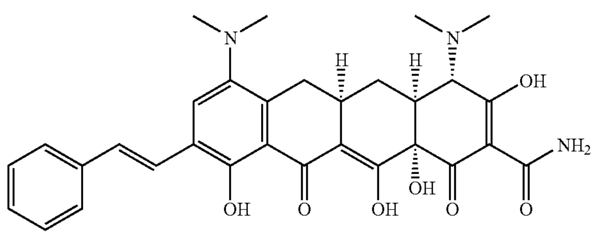 | * | * | ** |
| KC | 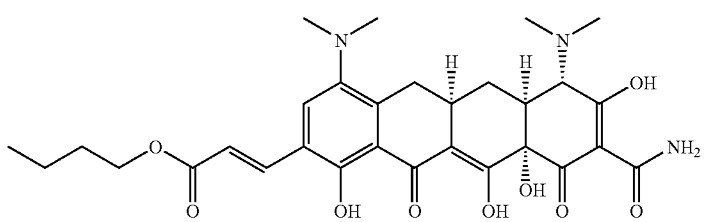 |  |  | * |
| KD | 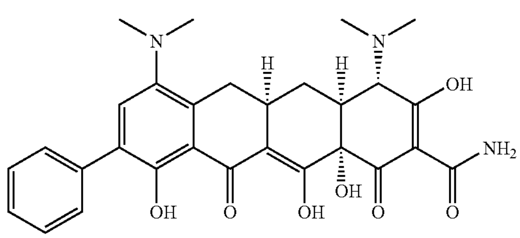 |  |  | * |
| KE | 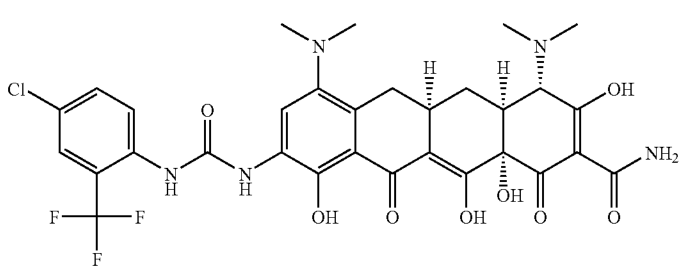 |  | * | * |

TABLE 1-continued

| ID | STRUCTURE | S. aureus | E. hirae | E. coli |
|---|---|---|---|---|
| KF | 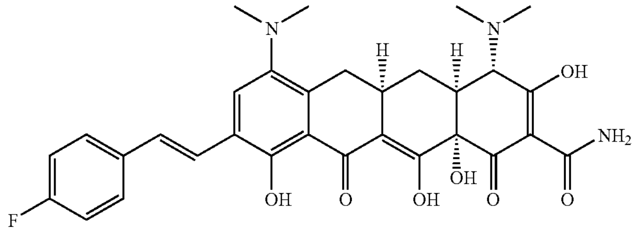 | * | * | * |
| KH | 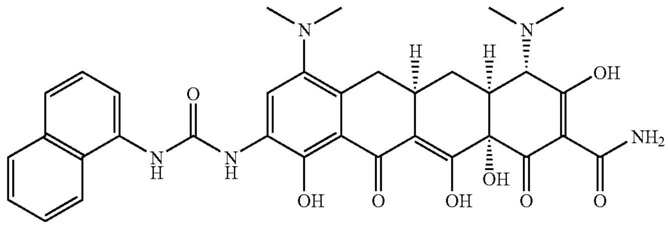 |  |  | ** |
| KI | 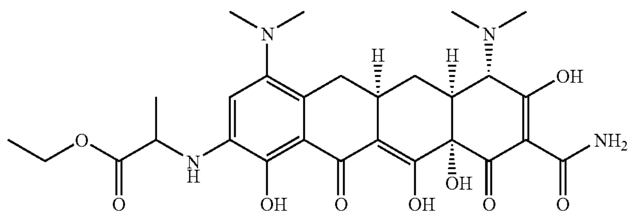 |  |  | * |
| KJ | 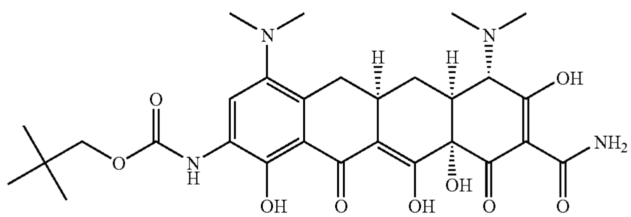 |  |  | * |
| KK | 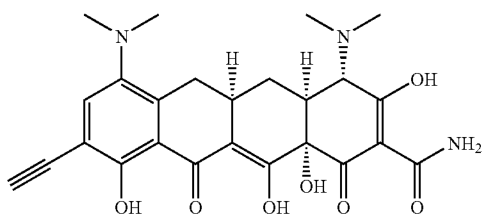 |  |  | ** |
| KL | 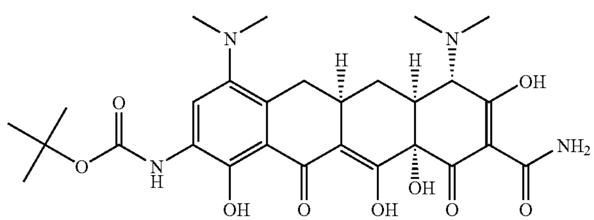 |  |  | * |
| KM | 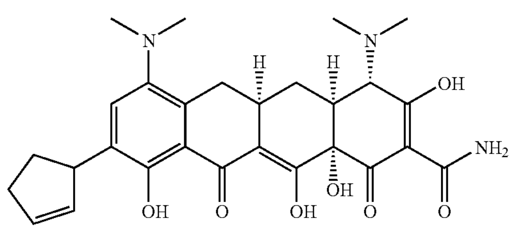 |  |  | ** |

TABLE 1-continued

| ID | STRUCTURE | S. aureus | E. hirae | E. coli |
|----|-----------|-----------|----------|---------|
| KN | 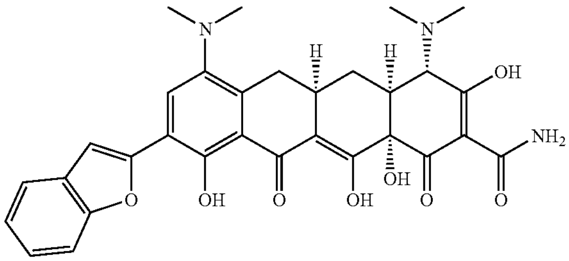 | * |  | ** |
| KO | 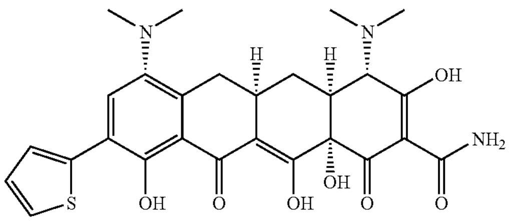 |  |  | ** |
| KP | 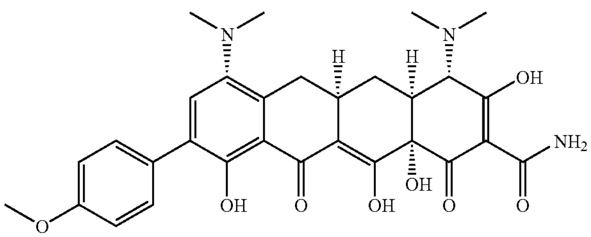 |  |  | * |
| KQ | 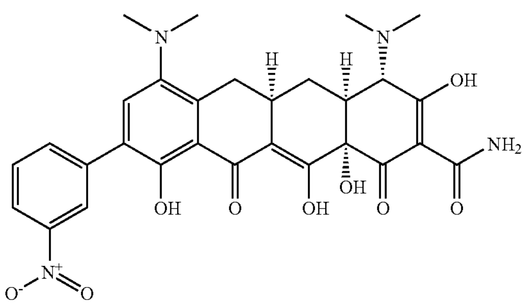 |  |  | ** |
| KR | 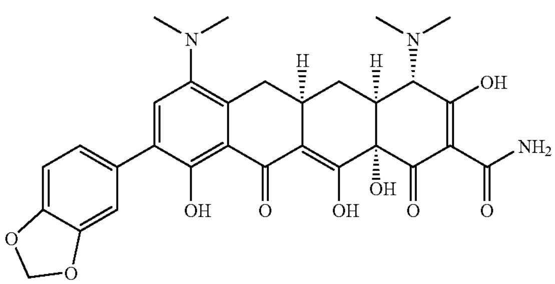 |  |  | ** |
| KS | 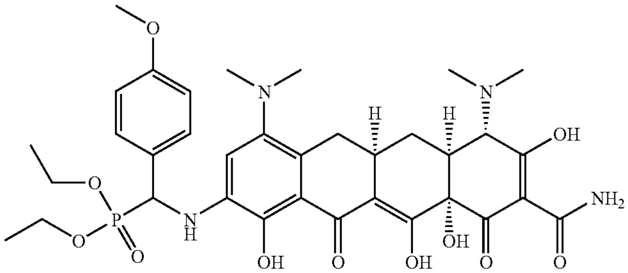 | * | * | ** |

TABLE 1-continued
| ID | STRUCTURE | S. aureus | E. hirae | E. coli |
|---|---|---|---|---|
| KT | 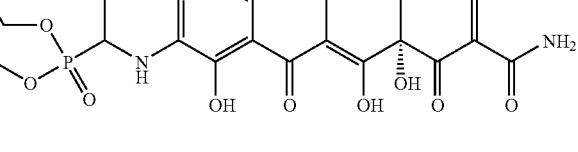 | * | * | * |
| KU | 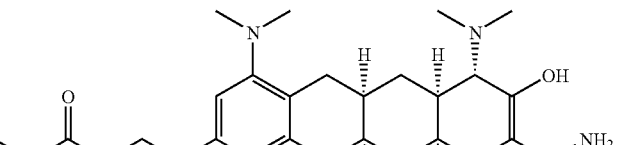 | ** | * | *** |
| KV | 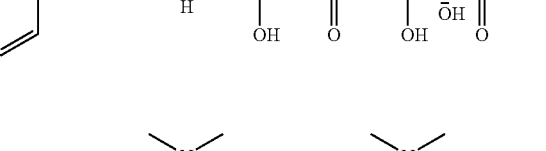 |  |  | ** |
| KW | 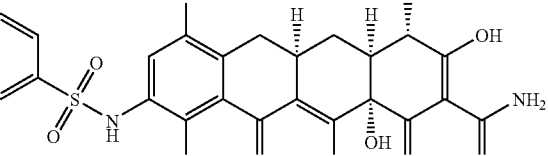 |  |  | * |
| KX | 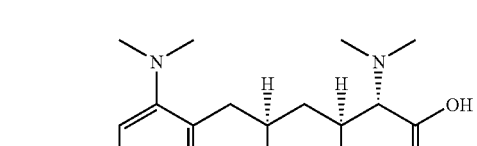 |  |  | * |
| KY | 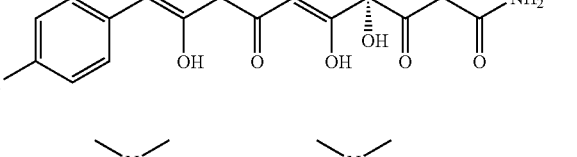 | * | * | * |

TABLE 1-continued

| ID | STRUCTURE | S. aureus | E. hirae | E. coli |
|---|---|---|---|---|
| KZ | 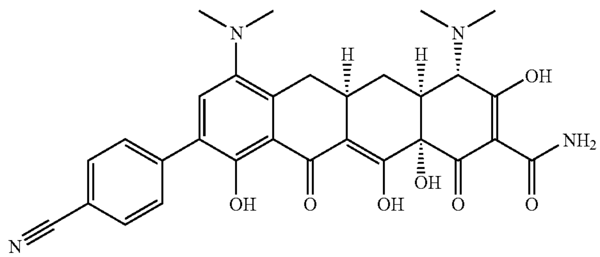 |  |  | * |
| LA | 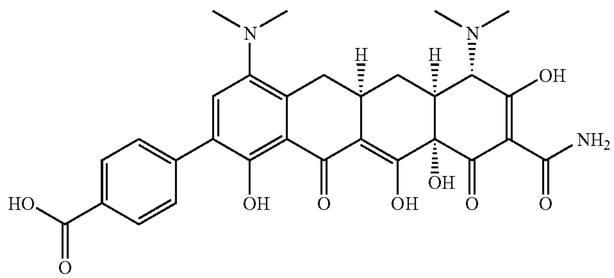 |  |  | * |
| LB | 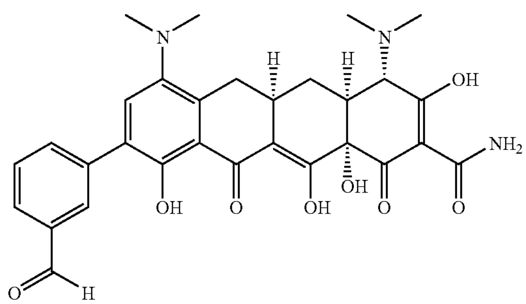 |  |  | * |
| LC | 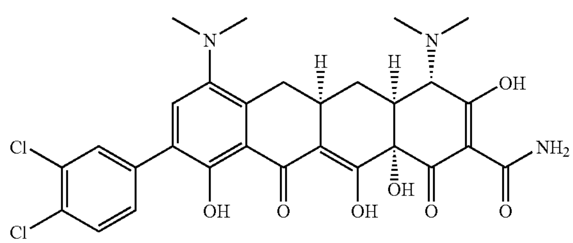 |  |  | * |
| LD | 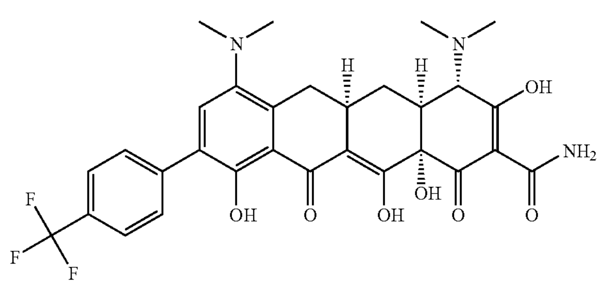 |  | * | * |

TABLE 1-continued

| ID | STRUCTURE | S. aureus | E. hirae | E. coli |
|---|---|---|---|---|
| LE | 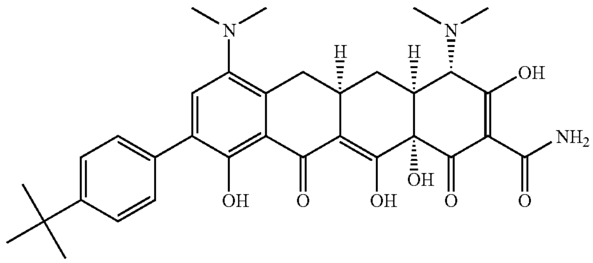 |  |  | * |
| LF | 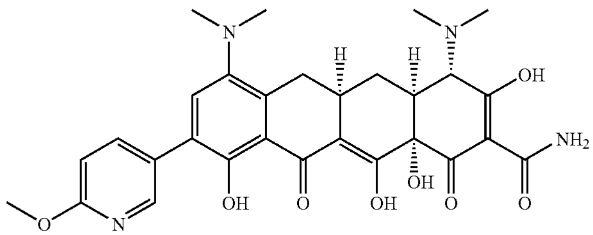 | * | * | * |
| LG | 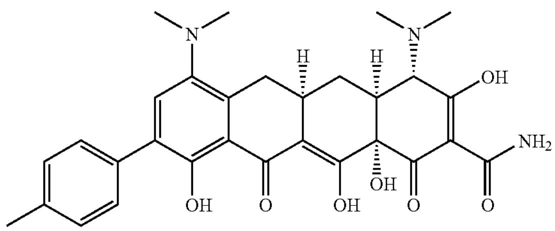 |  |  | * |
| LH | 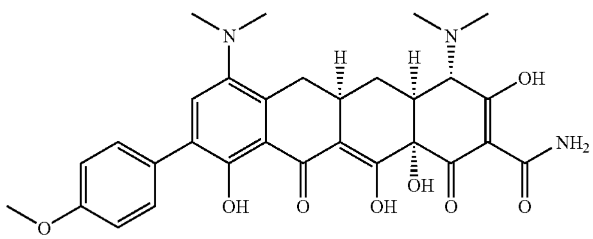 |  |  | * |
| LI | 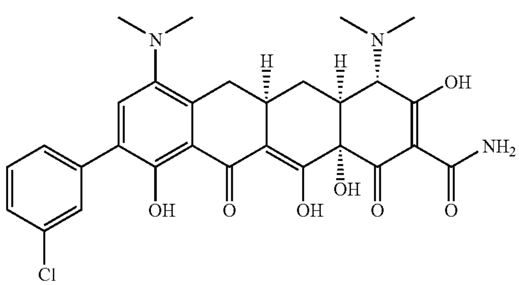 |  |  | * |
| LJ | 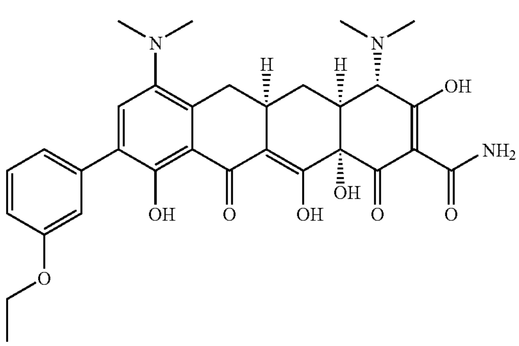 |  |  | * |

TABLE 1-continued
| ID | STRUCTURE | S. aureus | E. hirae | E. coli |
|----|-----------|-----------|----------|---------|
| LK | 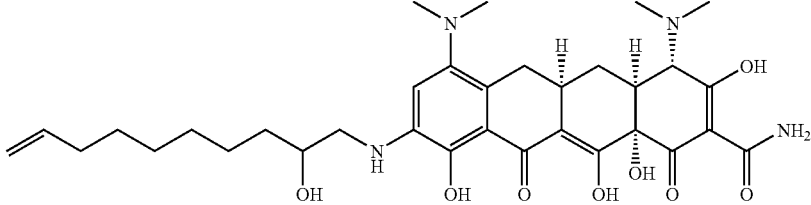 | ** | * | * |
| LM | 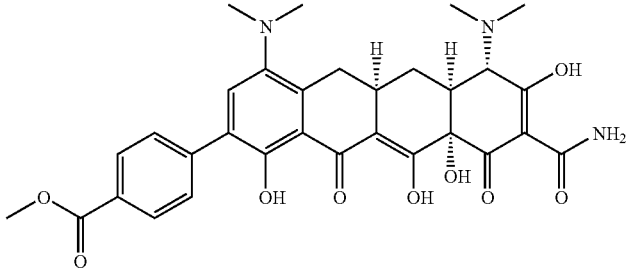 |  |  | * |
| LN | 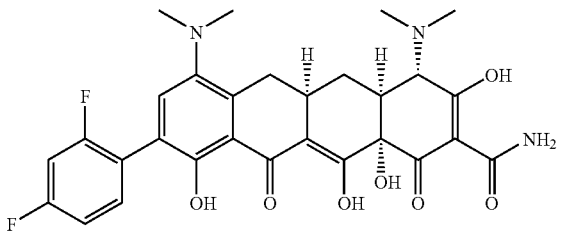 |  |  | * |
| LO | 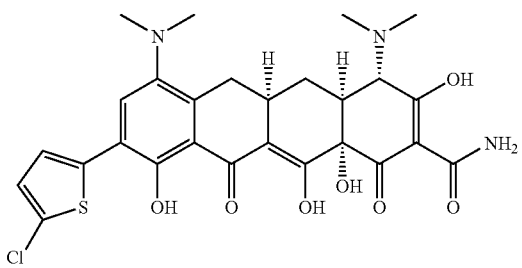 |  |  | * |
| LP | 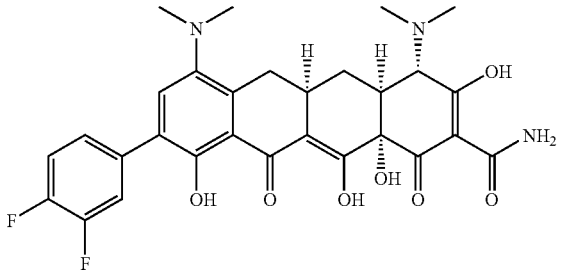 |  |  | ** |
| LQ | 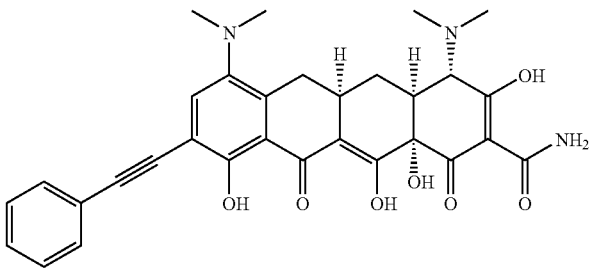 | * | * | * |

TABLE 1-continued
| ID | STRUCTURE | S. aureus | E. hirae | E. coli |
|---|---|---|---|---|
| LR | 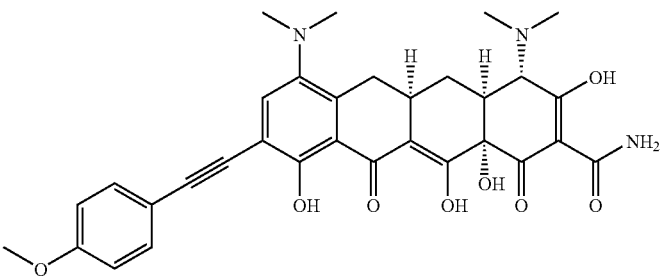 |  |  | ** |
| LS | 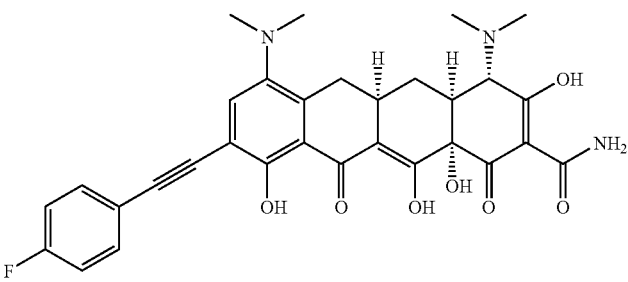 |  |  | ** |
| LT | 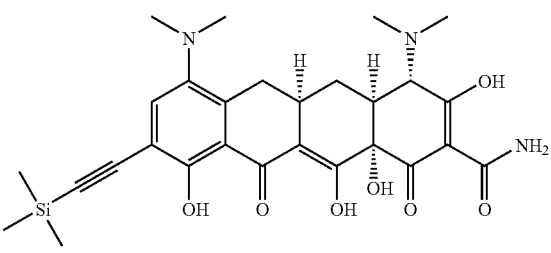 |  |  | ** |
| LU | 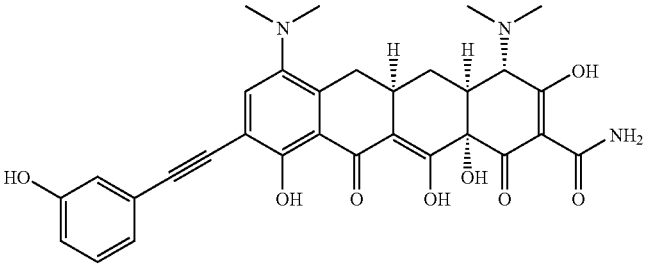 |  |  | * |
| LV | 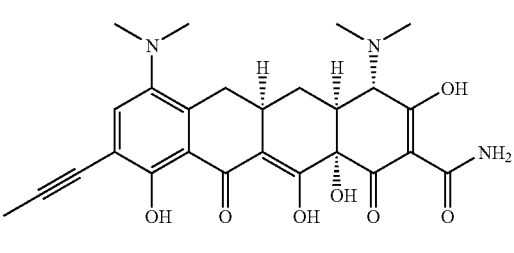 | * | * | * |
| LW | 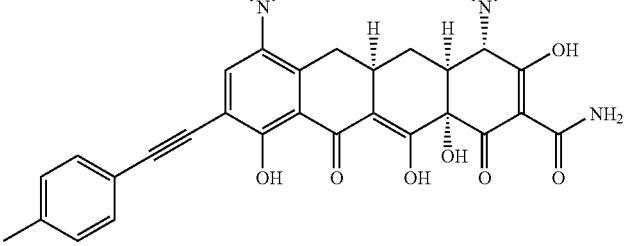 |  |  | ** |

TABLE 1-continued

| ID | STRUCTURE | S. aureus | E. hirae | E. coli |
|---|---|---|---|---|
| LX | 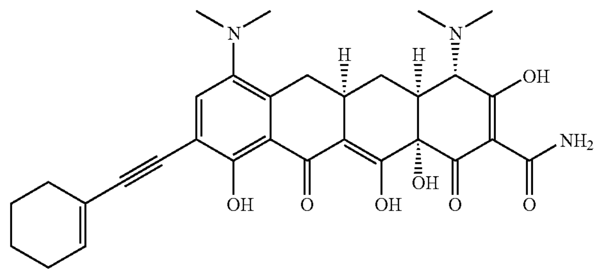 |  |  | * |
| LY | 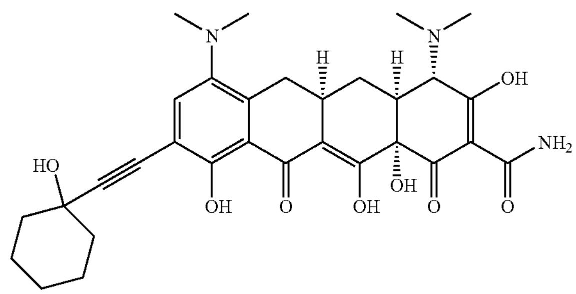 | * | * | * |
| LZ | 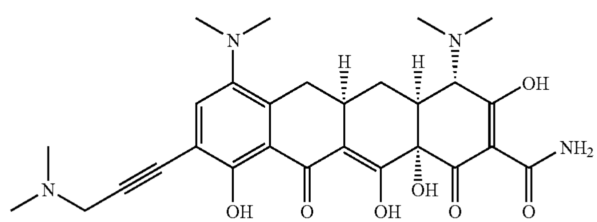 | * | * | * |
| MA | 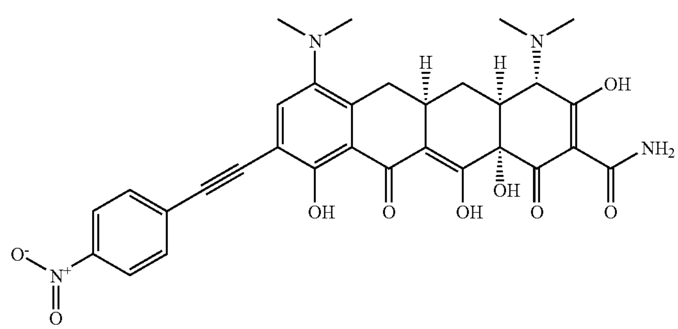 |  |  | * |
| MB | 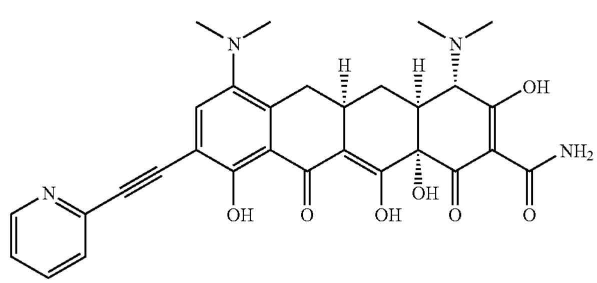 | * | * | * |

TABLE 1-continued

| ID | STRUCTURE | S. aureus | E. hirae | E. coli |
|---|---|---|---|---|
| MC | 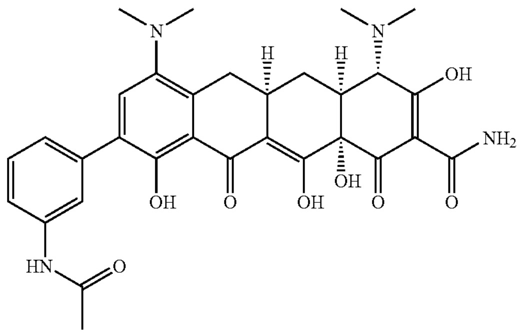 | * | * | * |
| MD | 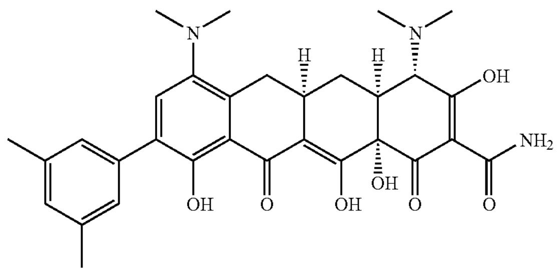 |  |  | ** |
| ME | 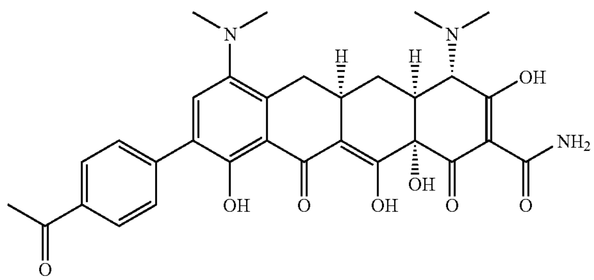 | * | ** | * |
| MF | 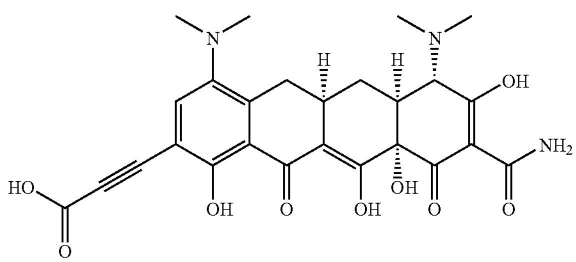 | * | * | * |
| MG | 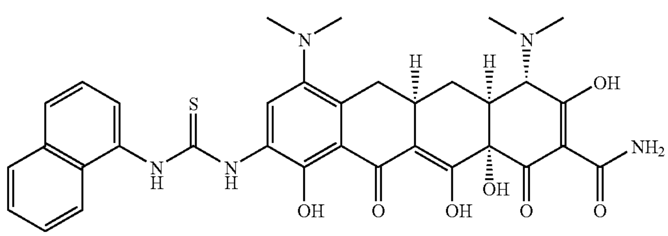 |  |  | * |
| MH | 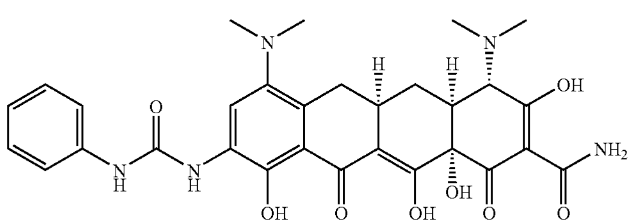 |  |  | ** |

TABLE 1-continued

| ID | STRUCTURE | S. aureus | E. hirae | E. coli |
|----|-----------|-----------|----------|---------|
| MI | 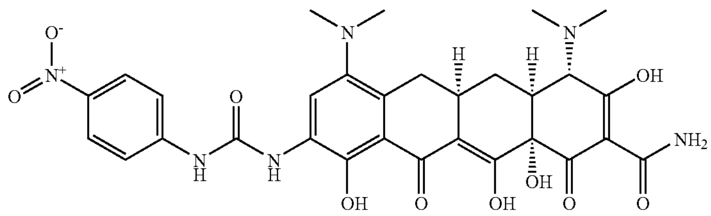 |  |  | * |
| MK | 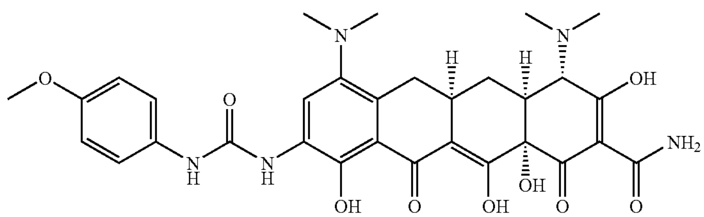 | * |  |  |
| ML | 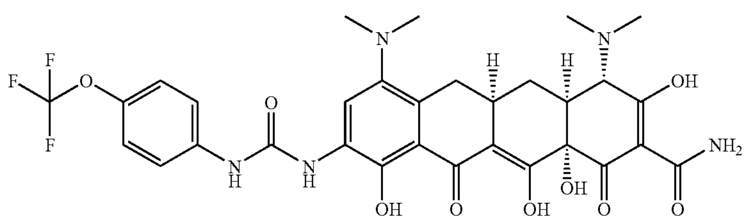 |  |  | ** |
| MM | 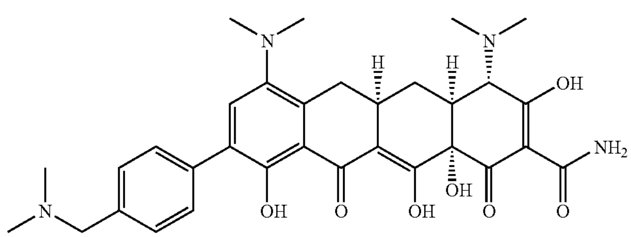 | ** | * | ** |
| MN | 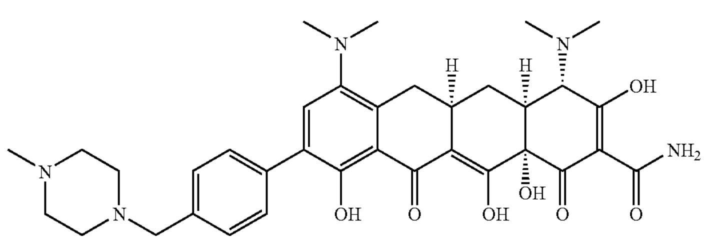 | * | * | * |
| MO | 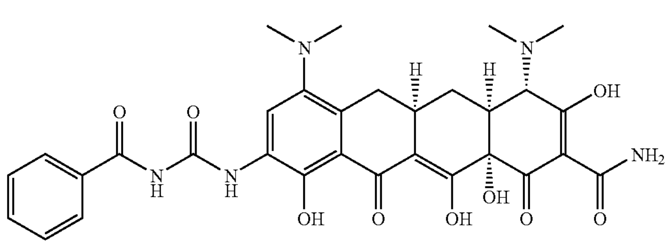 |  |  | * |

TABLE 1-continued

| ID | STRUCTURE | S. aureus | E. hirae | E. coli |
|----|-----------|-----------|----------|---------|
| MP | 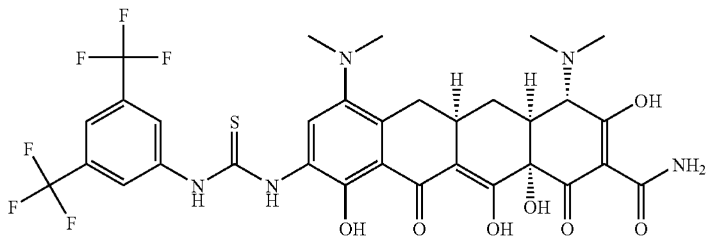 |  |  | ** |
| MQ | 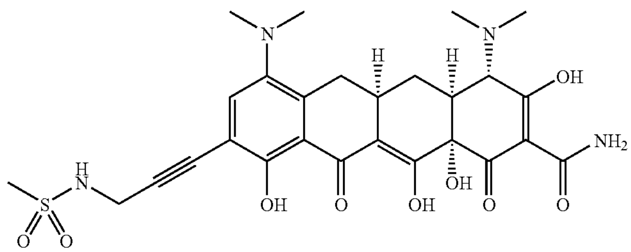 | * | * | * |
| MR | 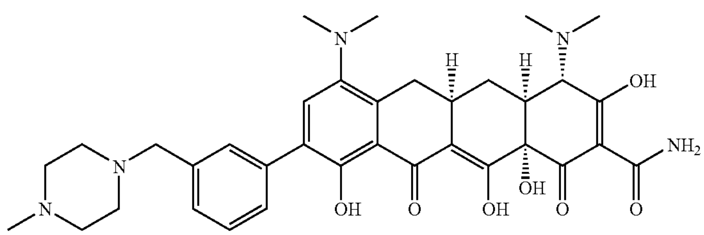 | * | ** | * |
| MS | 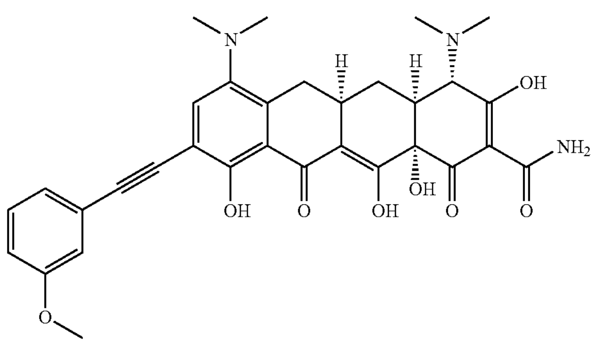 | * | * | ** |
| MT | 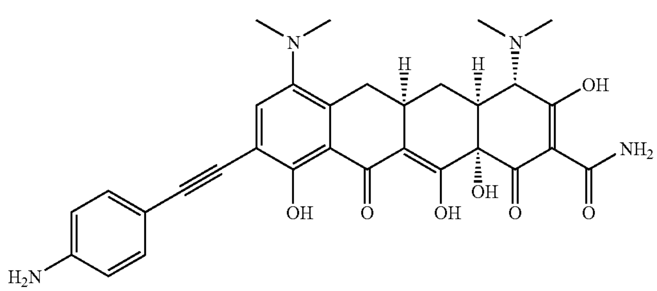 | * | * | * |

TABLE 1-continued

| ID | STRUCTURE | S. aureus | E. hirae | E. coli |
|----|-----------|-----------|----------|---------|
| MU | 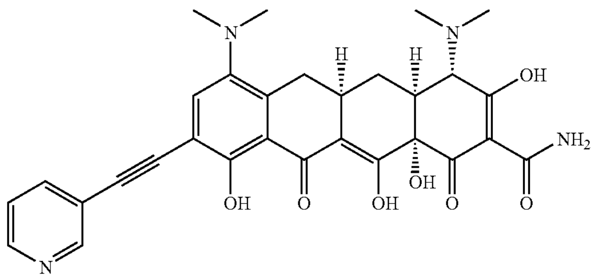 |  |  | * |
| MV | 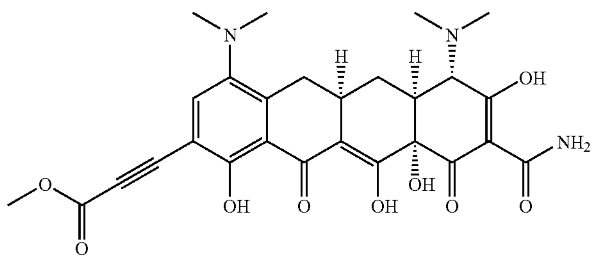 |  |  | * |
| MW | 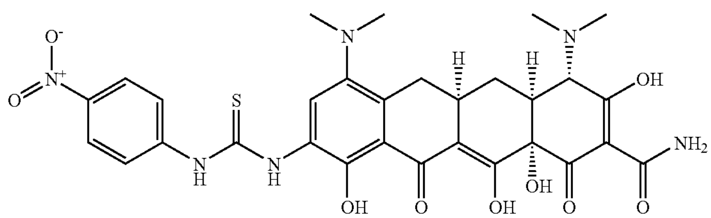 |  |  | * |
| MX | 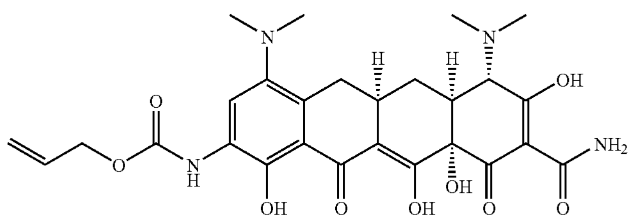 |  |  | * |
| MY | 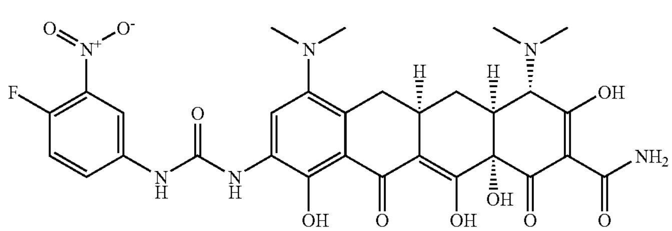 |  |  | * |
| MZ | 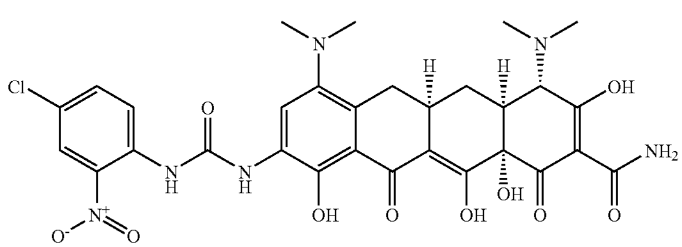 |  |  | ** |

TABLE 1-continued
| ID | STRUCTURE | S. aureus | E. hirae | E. coli |
|----|-----------|-----------|----------|---------|
| NA | 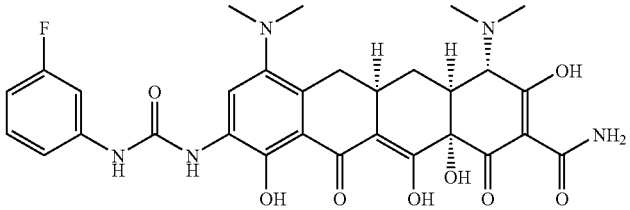 |  |  | |
| NB | 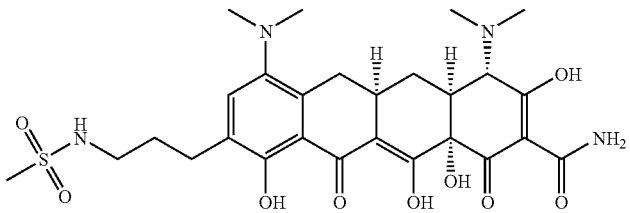 | * | * | * |
| NC | 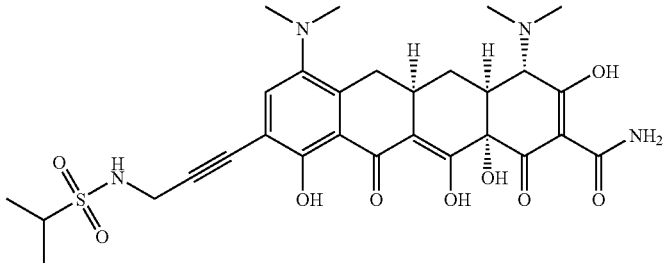 | * | * | * |
| ND | 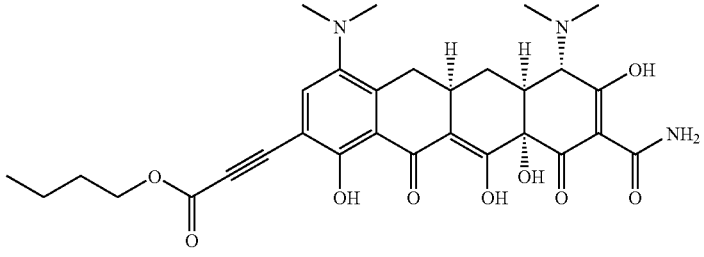 | * | * | * |
| NE | 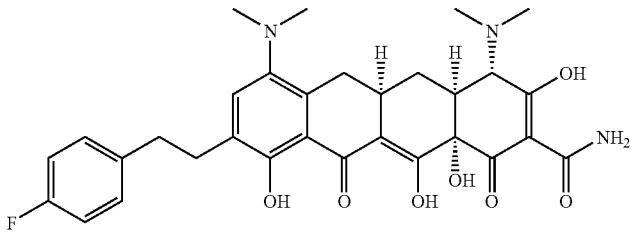 | * | * | *** |
| NF | 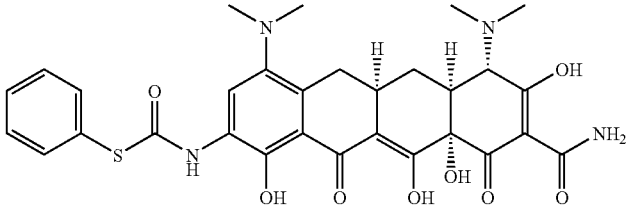 | * | * | * |

TABLE 1-continued

| ID | STRUCTURE | S. aureus | E. hirae | E. coli |
|----|-----------|-----------|----------|---------|
| NG | 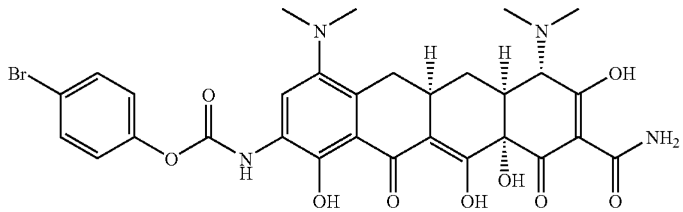 | * | * | * |
| NH | 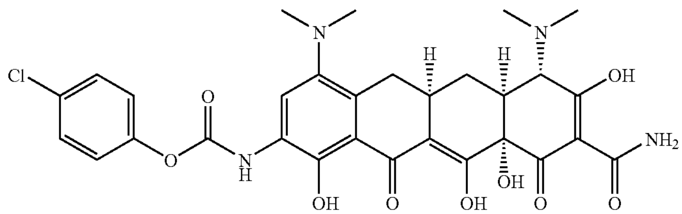 | * | * | * |
| NI | 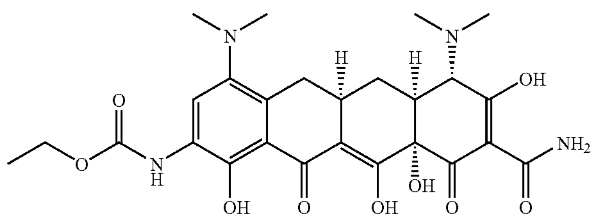 | * |  | ** |
| NJ | 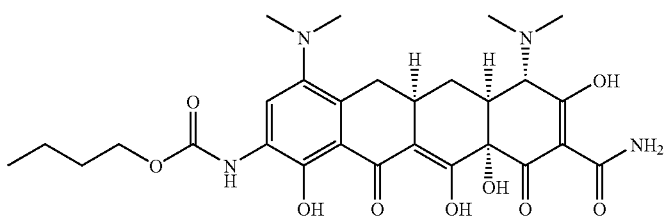 |  |  | ** |
| NK | 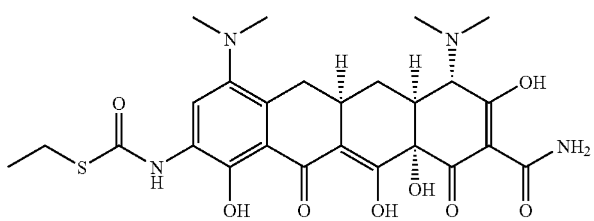 |  |  | * |
| NL | 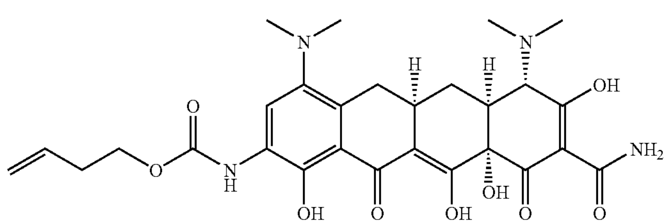 |  |  | ** |
| NM | 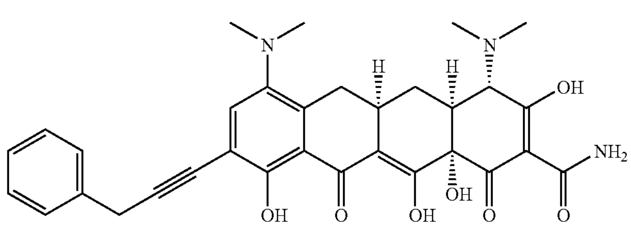 |  |  | ** |

TABLE 1-continued

| ID | STRUCTURE | S. aureus | E. hirae | E. coli |
|---|---|---|---|---|
| NO | 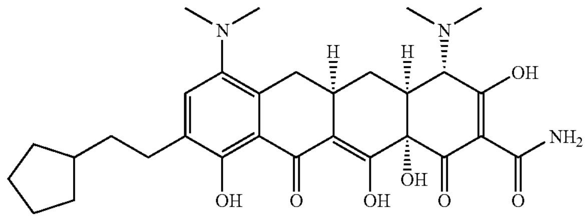 |  |  | ** |
| NP | 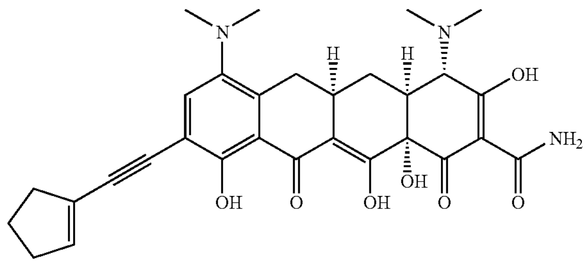 |  |  | ** |
| NQ | 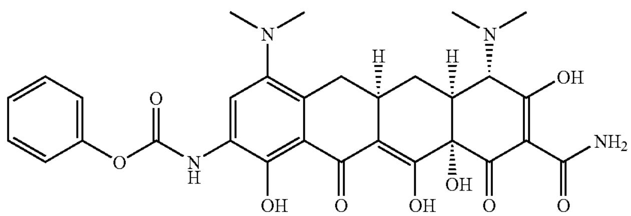 | * | * | * |
| NR | 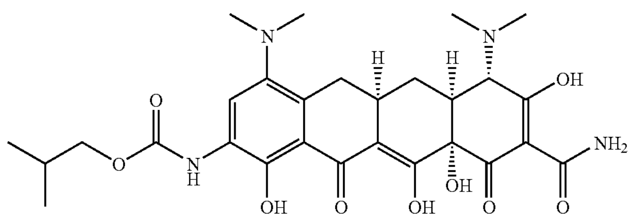 |  |  | ** |
| NS | 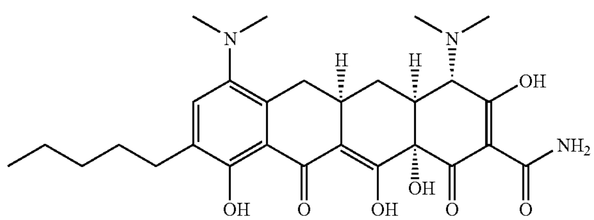 |  |  | ** |
| NT | 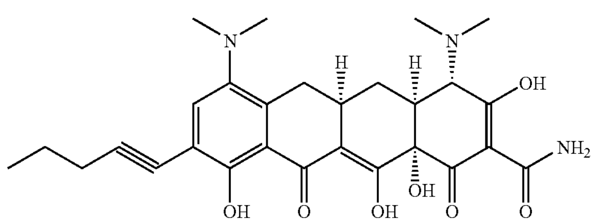 |  |  | ** |
| NU | 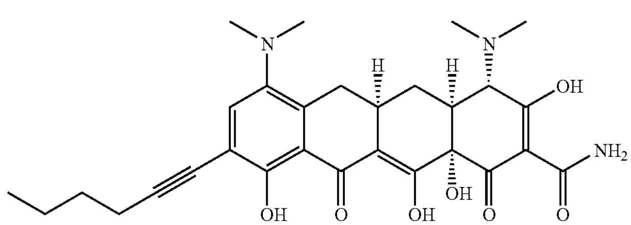 | * | * | *** |

TABLE 1-continued
| ID | STRUCTURE | S. aureus | E. hirae | E. coli |
|---|---|---|---|---|
| NV | 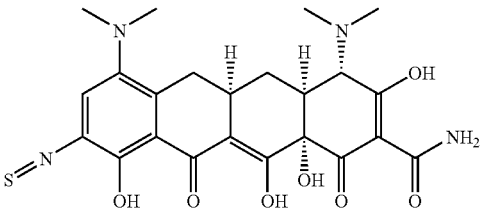 | * | * | * |
| NW | 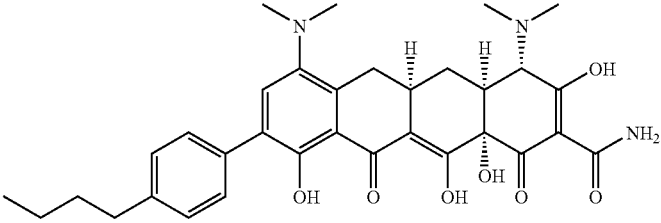 | * | *** | * |
| NX | 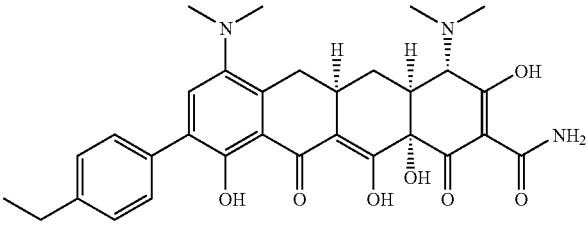 | * | * | ** |
| NY | 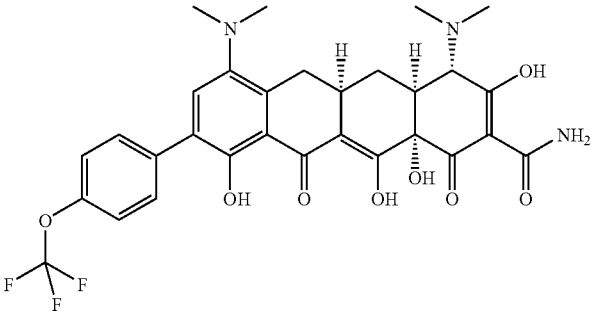 | * | *** | * |
| NZ | 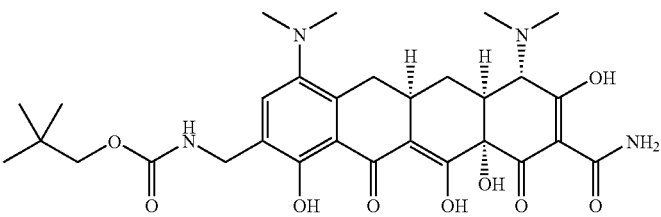 |  |  | * |
| OA | 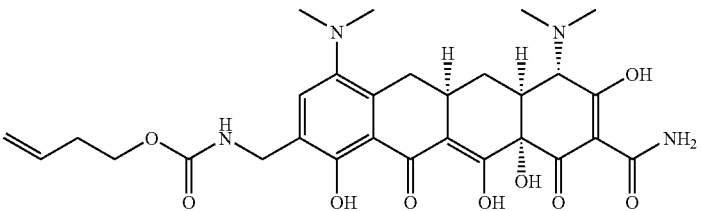 |  |  | * |

TABLE 1-continued
| ID | STRUCTURE | S. aureus | E. hirae | E. coli |
|---|---|---|---|---|
| OB | 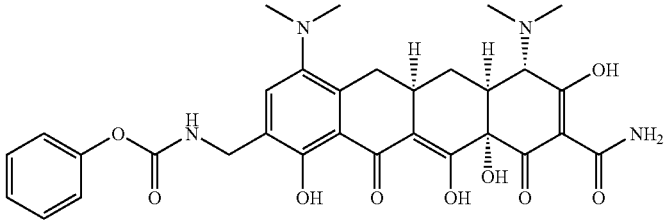 |  |  | * |
| OC | 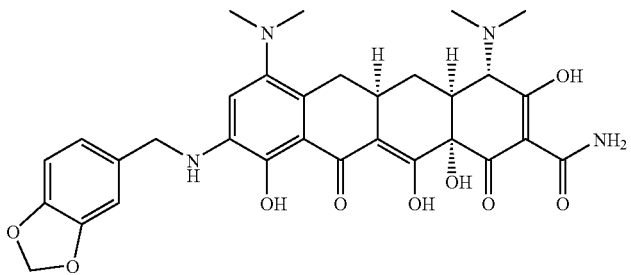 | * | * | * |
| OD | 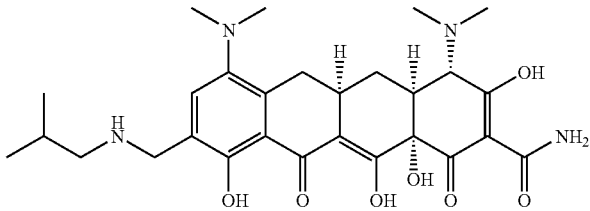 | * | NT | * |
| OE | 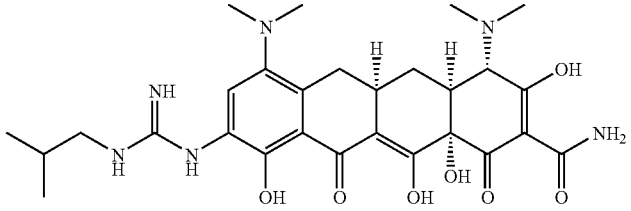 | * | * | * |
| OF | 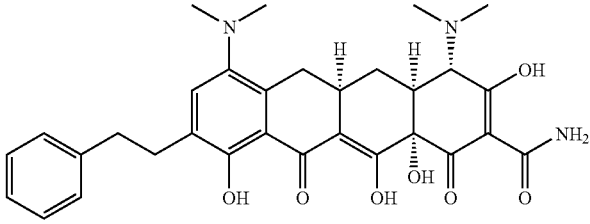 | * | NT | ** |
| OG | 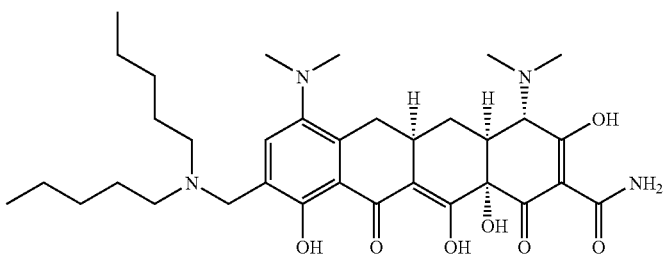 |  | NT |  |

TABLE 1-continued

| ID | STRUCTURE | S. aureus | E. hirae | E. coli |
|----|-----------|-----------|----------|---------|
| OH | 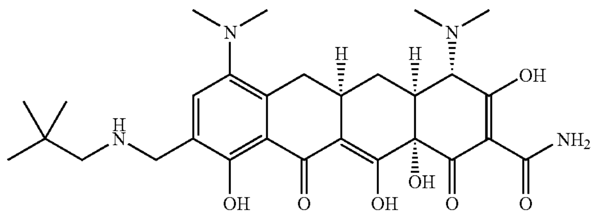 | * | NT | * |
| OI | 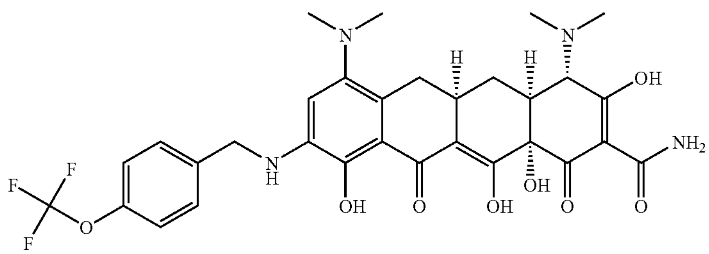 | ** | NT | * |
| OJ | 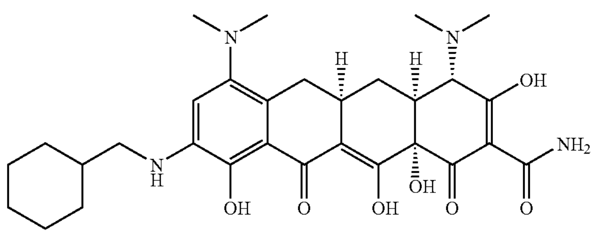 | ** | NT | * |
| OK | 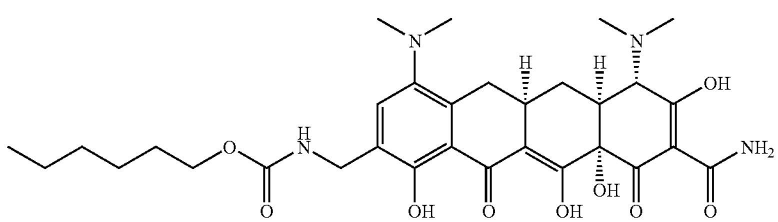 |  | NT |  |
| OL | 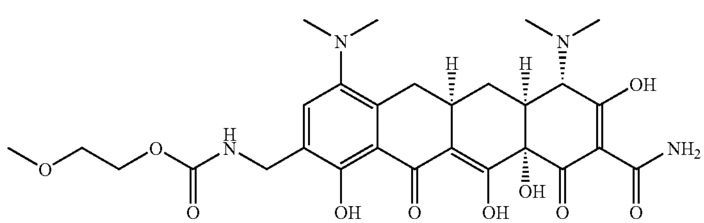 | * | NT | * |
| OM | 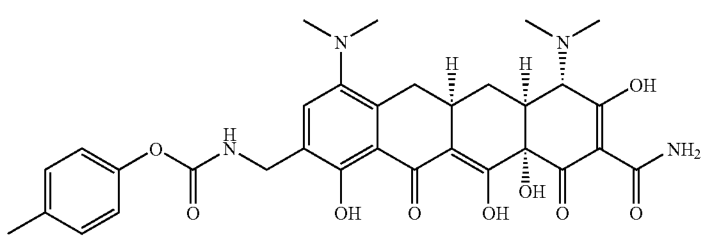 | ** | NT | * |

TABLE 1-continued
| ID | STRUCTURE | S. aureus | E. hirae | E. coli |
|----|-----------|-----------|----------|---------|
| ON | 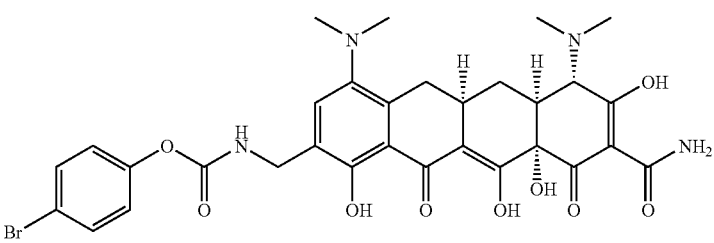 | ** | NT | * |
| OO | 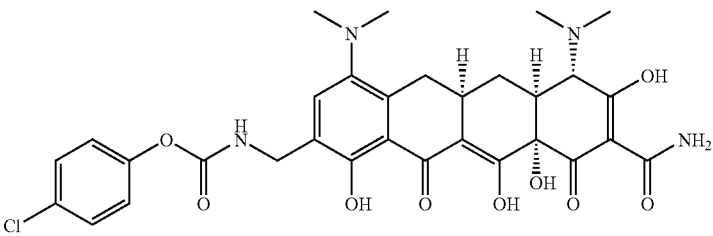 |  | NT |  |
| OP | 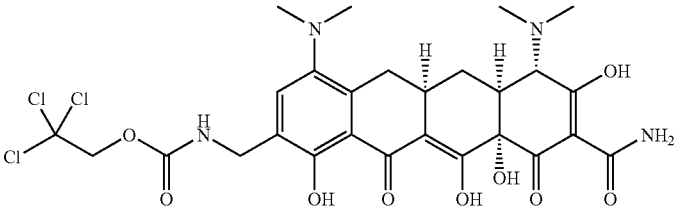 |  | NT |  |
| OQ | 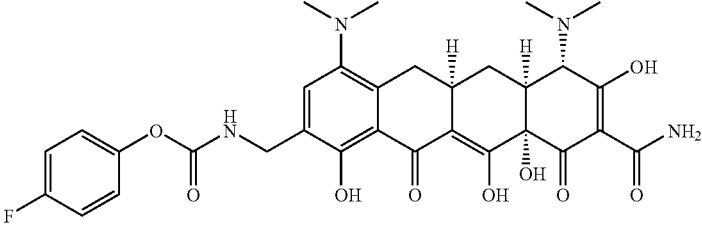 | ** | NT | * |
| OR | 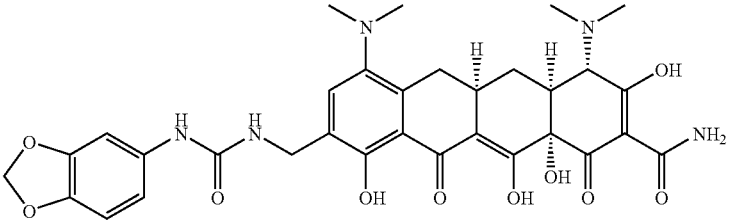 | * | NT | * |
| OS | 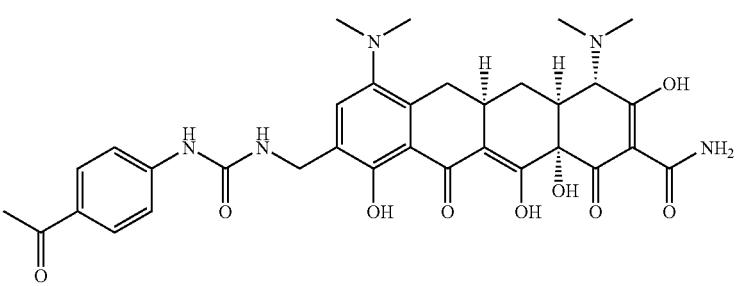 | * | NT | * |

TABLE 1-continued
| ID | STRUCTURE | S. aureus | E. hirae | E. coli |
|----|-----------|-----------|----------|---------|
| OT | 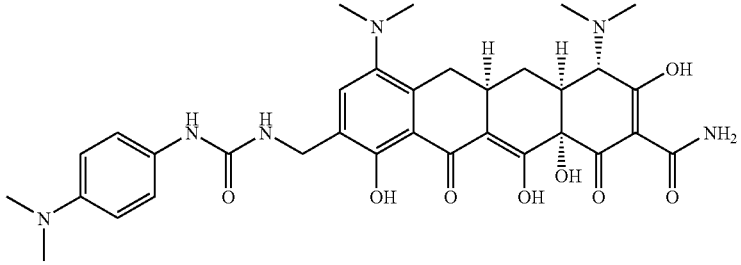 | * | NT | * |
| OU | 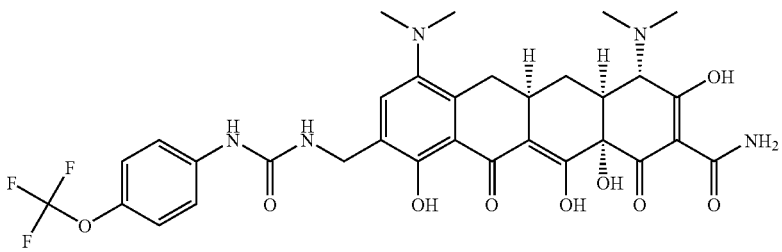 | ** | NT | * |
| OV | 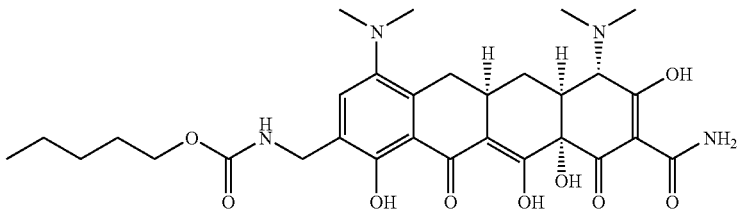 |  | NT |  |
| OW | 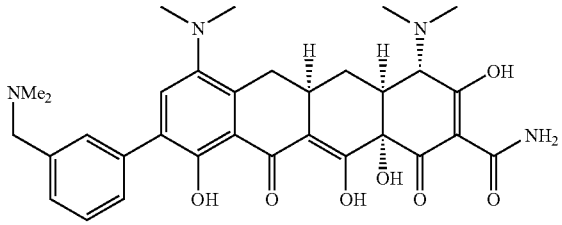 | NT | NT | NT |
| OX | 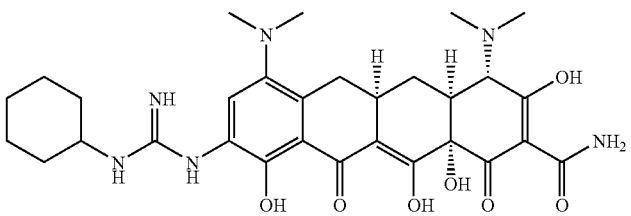 | NT | NT | NT |
| OY | 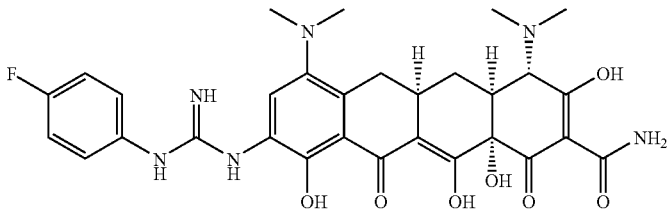 | NT | NT | NT |

TABLE 1-continued

| ID | STRUCTURE | S. aureus | E. hirae | E. coli |
|----|-----------|-----------|----------|---------|
| OZ | 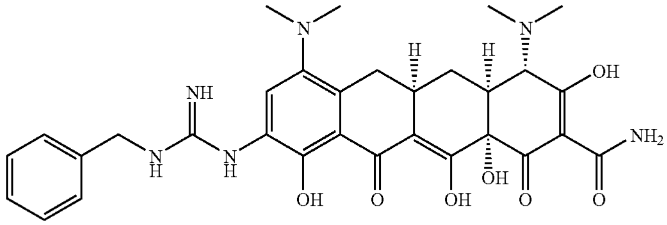 | NT | NT | NT |
| PA | 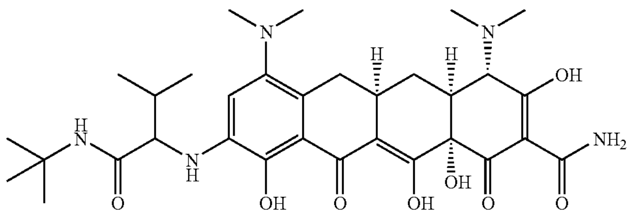 | NT | NT | NT |
| PB | 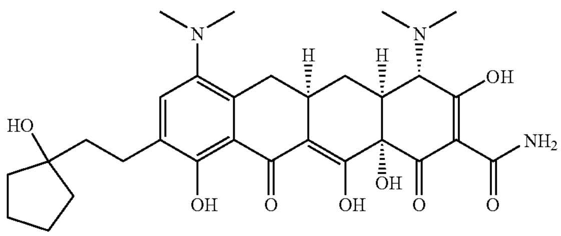 | NT | NT | NT |
| PC | 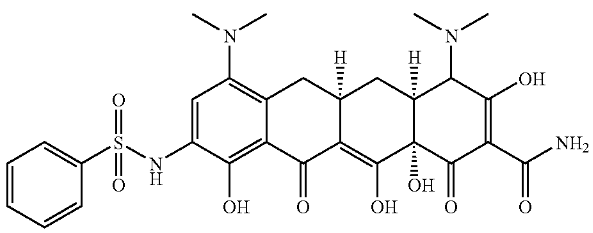 | NT | NT | NT |
| PD | 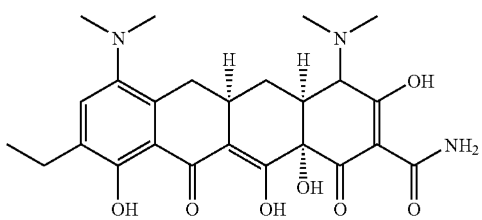 | NT | NT | NT |
| PE | 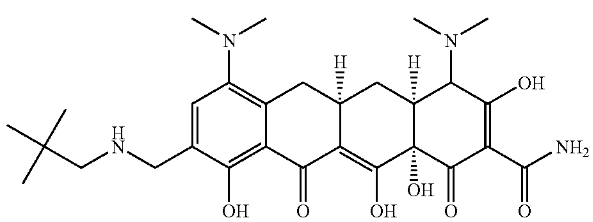 | NT | NT | NT |
| PF | 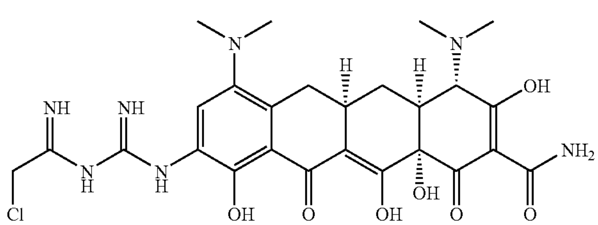 | NT | NT | NT |

TABLE 1-continued

| ID | STRUCTURE | S. aureus | E. hirae | E. coli |
|----|-----------|-----------|----------|---------|
| PG | 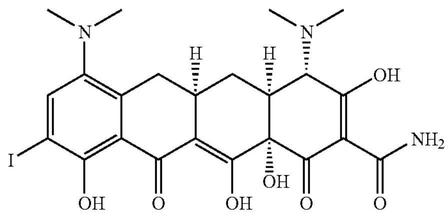 | NT | NT | NT |
| PH | 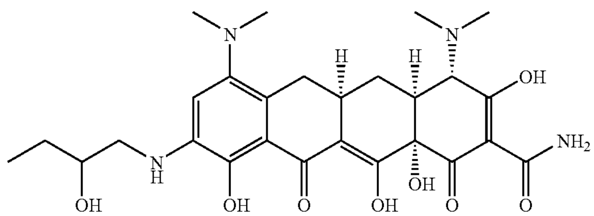 | NT | NT | NT |
| PI | 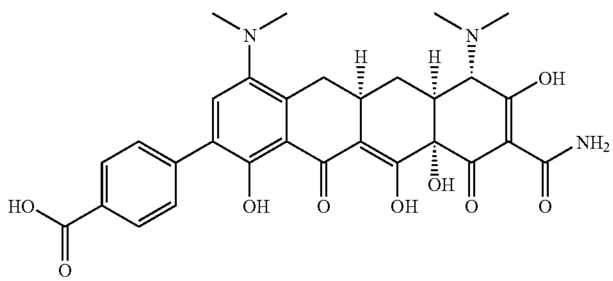 | NT | NT | NT |
| PJ | 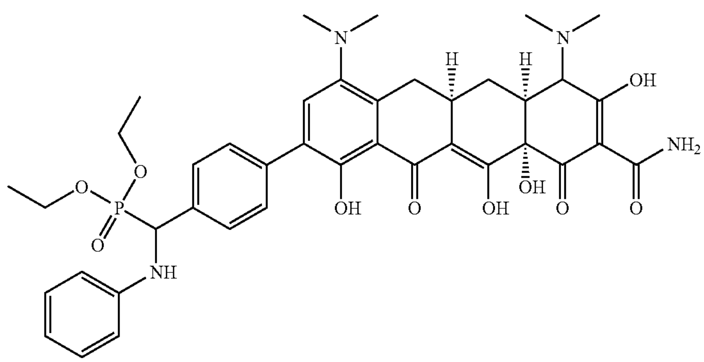 | NT | NT | NT |
| PK | 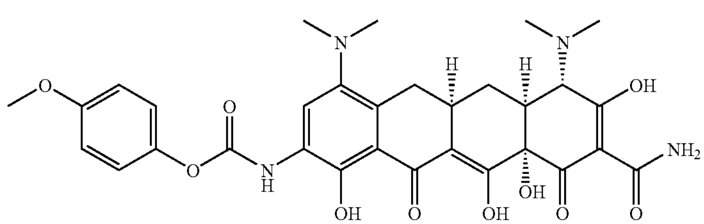 | NT | NT | NT |
| PL | 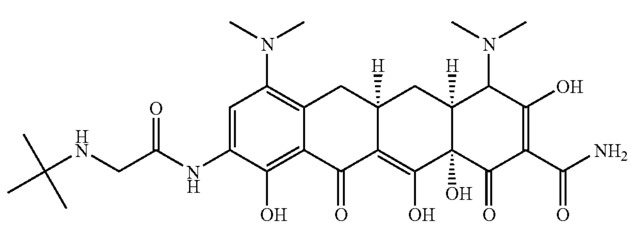 | NT | NT | NT |

TABLE 1-continued

| ID | STRUCTURE | S. aureus | E. hirae | E. coli |
|---|---|---|---|---|
| PM | 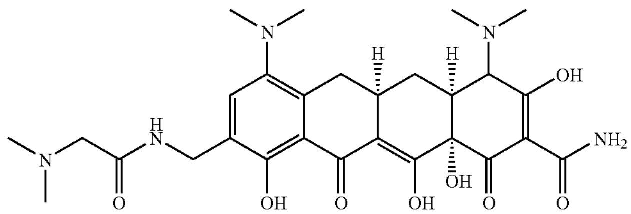 | NT | NT | NT |
| PN | 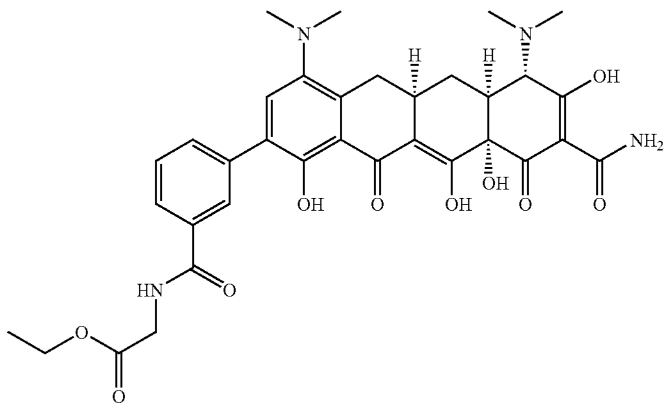 | NT | NT | NT |
| PO | 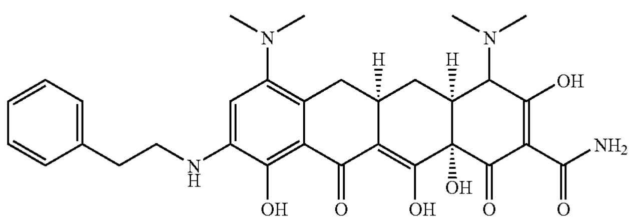 | NT | NT | NT |
| PP | 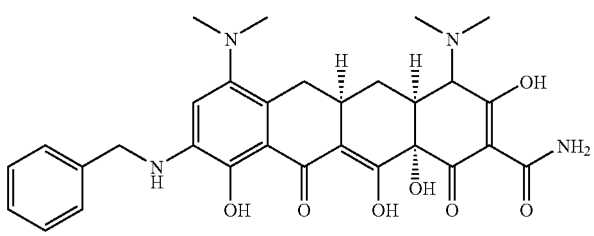 | NT | NT | NT |
| PQ | 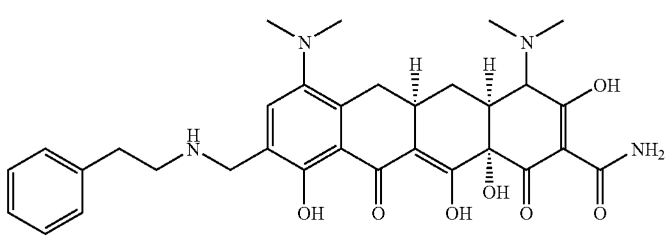 | NT | NT | NT |
| PR | 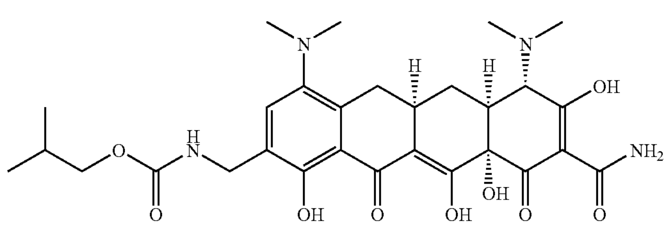 | NT | NT | NT |

TABLE 1-continued
| ID | STRUCTURE | S. aureus | E. hirae | E. coli |
|----|-----------|-----------|----------|---------|
| PS | 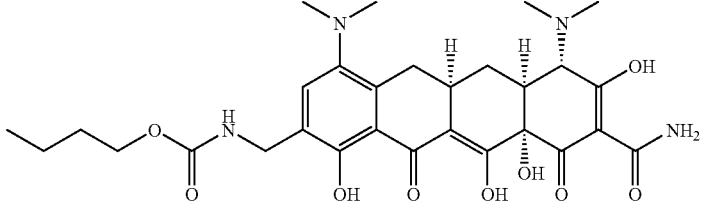 | NT | NT | NT |
| PT | 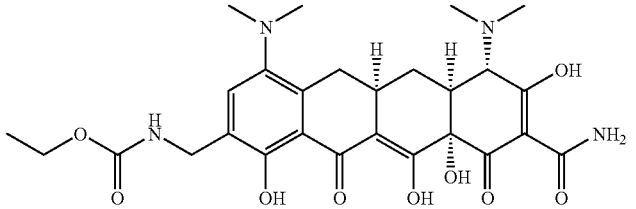 | NT | NT | NT |
| PU | 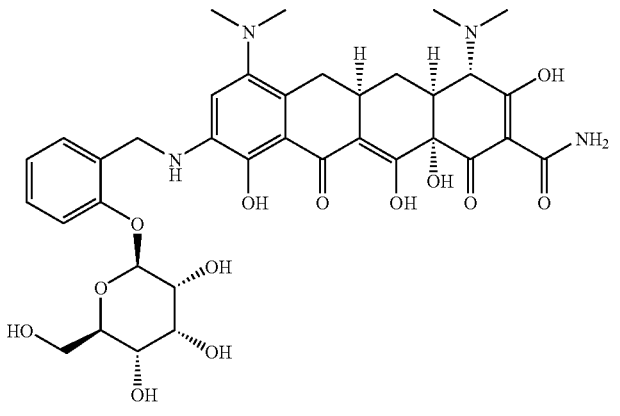 | NT | NT | NT |
| PV | 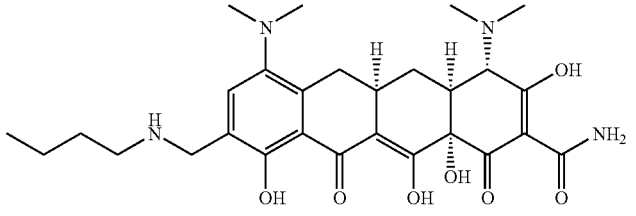 | NT | NT | NT |
| PW | 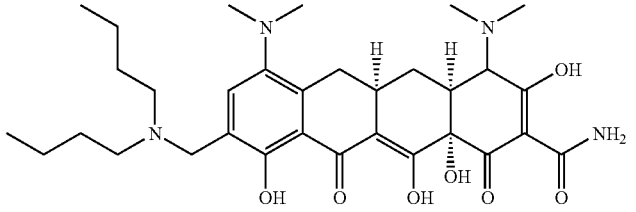 | NT | NT | NT |
| PX | 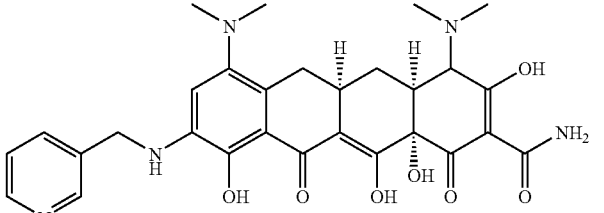 | NT | NT | NT |

The invention claimed is:

1. A minocycline compound of formula I:

$$\text{(I)}$$

wherein:
X is $CHC(R^{13}Y'Y)$ or $CR^6R^{6'}$;
$R^2$, $R^{4'}$ and $R^{4''}$ are each independently hydrogen, alkyl, alkenyl, alkynyl, alkoxy, alkylthio, alkylsulfinyl, alkylsulfonyl, alkylamino, arylalkyl, aryl, heterocyclic, or heteroaromatic;
$R^{7'}$ and $R^{7''}$ are each independently alkyl;
$R^4$ is $NR^{4'}R^{4''}$, alkyl, alkenyl, alkynyl, aryl, hydroxyl, or halogen;
$R^{2'}$, $R^3$, $R^{10}$, $R^{11}$ and $R^{12}$ are each hydrogen;
$R^5$ is hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, hydroxyl, halogen, thiol, alkyl, alkenyl, alkynyl, aryl, alkoxy, alkylthio, alkylsulfinyl, alkylsulfonyl, alkylamino, or arylalkyl;
$R^9$ is an unsubstituted single-ring aromatic group having zero heteroatoms or a single-ring aromatic group having zero heteroatoms substituted with alkyl, alkenyl, alkynyl, aryl, halogen, hydroxyl, alkoxy, formyl, alkylcarbonyloxy, arylcarbonyloxy, alkoxycarbonyloxy, aryloxycarbonyloxy, carboxylate, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, amino, alkylamino, dialkylamino, arylamino, diarylamino, alkylarylamino, acylamino, alkylcarbonylamino, arylcarbonylamino, carbamoyl, ureido, amidino, imino, sulfhydryl, alkylthio, arylthio, thiocarboxylate, sulfate, alkylsulfinyl, sulfonato, sulfamoyl, sulfonamido, nitro, trifluoromethyl, cyano, azido, heterocyclyl, alkylaryl, aryl or a heteroaryl;
$R^8$ is hydrogen, hydroxyl, halogen, thiol, alkyl, alkenyl, alkynyl, aryl, alkoxy, alkylthio, alkylsulfinyl, alkylsulfonyl, alkylamino, or arylalkyl;
$R^{13}$ is hydrogen, hydroxy, alkyl, alkenyl, alkynyl, alkoxy, alkylthio, alkylsulfinyl, alkylsulfonyl, alkylamino, or arylalkyl; and
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or arylalkyl, or pharmaceutically acceptable salts or esters thereof.

2. The minocycline compound of claim 1, wherein $R^4$ is $NR^{4'}R^{4''}$; X is $CR^6R^{6'}$; $R^2$, $R^5$, $R^6$, $R^{6'}$ and $R^8$, are each hydrogen; and $R^{4'}$, $R^{4''}$, $R^{7'}$ and $R^{7''}$ are each lower alkyl.

3. The minocycline compound of claim 2, wherein $R^{4'}$, $R^{4''}$, $R^{7'}$, and $R^{7''}$ are each methyl.

4. The minocycline compound of claim 1, wherein $R^9$ is unsubstituted phenyl.

5. The minocycline compound of claim 1, wherein $R^9$ is phenyl substituted with one or more substituents selected from the group consisting of alkyl, alkenyl, alkynyl, aryl, halogen, hydroxyl, alkoxy, formyl, alkylcarbonyloxy, arylcarbonyloxy, carboxyl, alkoxycarbonyloxy, aryloxycarbonyloxy, carboxylate, alkylaminocarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, amino, acylamino, amido, imino, sulfhydryl, alkylthio, arylthio, thiocarboxylate, alkylsulfinyl, sulfonato, sulfamoyl, sulfonamido, nitro, trifluoromethyl, cyano, azido, heterocyclyl, alkylaryl, aryl and a heteroaryl.

6. The minocycline compound of claim 5, wherein said phenyl is substituted with one or more substituents selected from the group consisting of carboxylate, alkyl, alkenyl, alkynyl, aryl, heterocyclic, cyano, amino, halogen, alkoxy, alkoxycarbonyl, amido, alkylcarbonyl, and nitro.

7. A method for treating a bacterial infection in a subject, comprising administering to said subject aminocycline compound of claim 1, such that said subject is treated, wherein said bacterial infection is caused by a gram-positive bacterium or a gram-negative bacterium and said gram-positive bacterium is selected from the group consisting of S. aureus, E. hirae and E. faecalis and said gram-negative bacterium is selected from the group consisting of E. coli, K. pneumoniae, Salmonella, A. baumanii, B. catarrhalis and P. aeruginosa.

8. The method of claim 7, wherein said bacterial infection is caused by E. coli.

9. The method of claim 7, wherein said bacterial infection is caused by S. aureus.

10. The method of claim 7, wherein said bacterial infection is caused by E. faecalis.

11. The method of claim 7, wherein said minocycline compound is administered with a pharmaceutically acceptable carrier.

12. The method of claim 7, wherein said subject is a human.

13. A pharmaceutical composition comprising a therapeutically effective amount of aminocycline compound of claim 1 and a pharmaceutically acceptable carrier.

14. A minocycline compound of the formula or a pharmaceutically acceptable salt thereof.

15. The minocycline compound of claim 1, wherein said compound is:

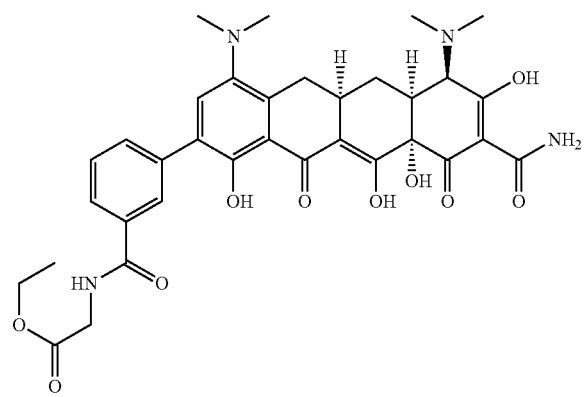

or a pharmaceutically acceptable salt thereof.

16. The minocycline compound of claim 1, wherein said compound is:

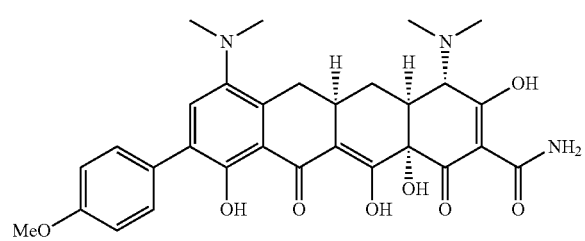

or a pharmaceutically acceptable salt thereof.

17. The minocycline compound of claim 1, wherein said compound is:

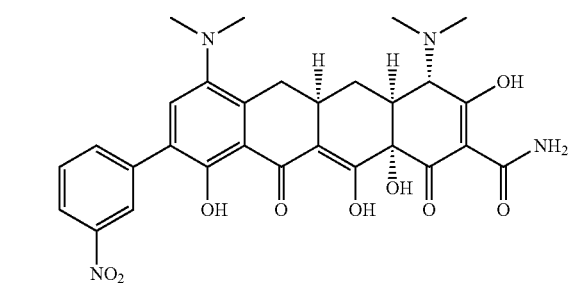

or a pharmaceutically acceptable salt thereof.

18. The minocycline compound of claim 1, wherein said compound is:

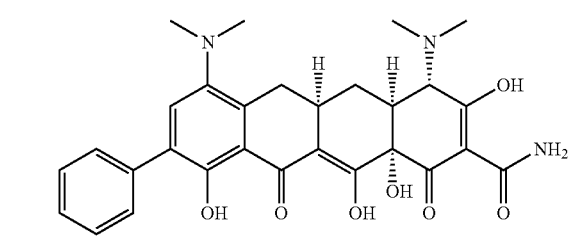

or a pharmaceutically acceptable salt thereof.

19. The minocycline compound of claim 1, wherein said compound is:

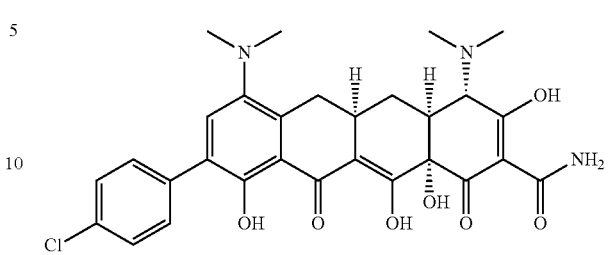

or a pharmaceutically acceptable salt thereof.

20. The minocycline compound of claim 1, wherein said compound is:

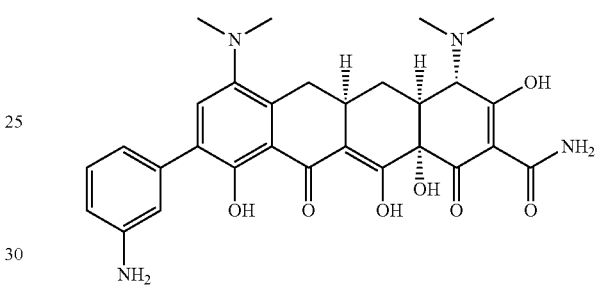

or a pharmaceutically acceptable salt thereof.

21. The minocycline compound of claim 1, wherein said compound is:

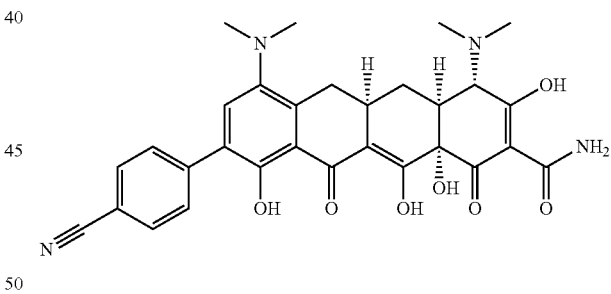

or a pharmaceutically acceptable salt thereof.

22. The minocycline compound of claim 1, wherein said compound is:

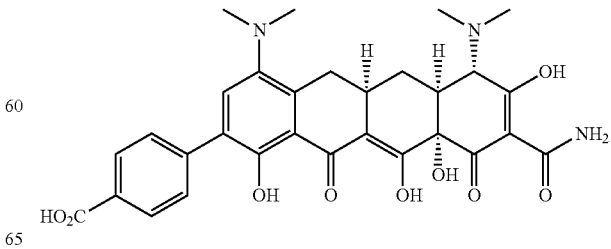

or a pharmaceutically acceptable salt thereof.

23. The minocycline compound of claim 1, wherein said compound is:

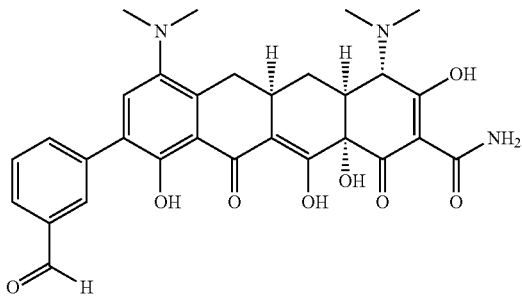

or a pharmaceutically acceptable salt thereof.

24. The minocycline compound of claim 1, wherein said compound is:

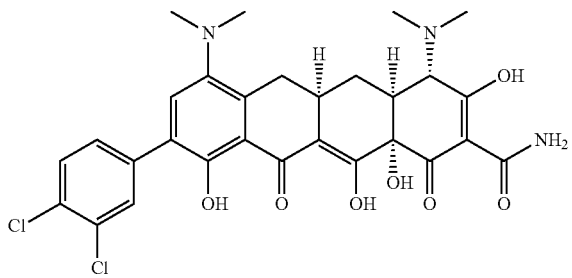

or a pharmaceutically acceptable salt thereof.

25. The minocycline compound of claim 1, wherein said compound is:

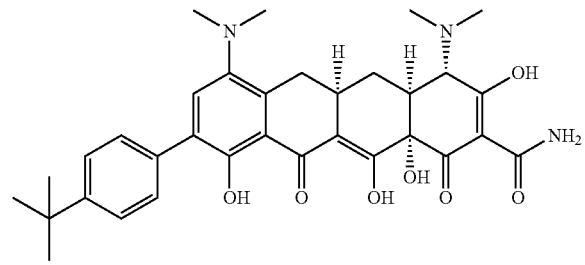

or a pharmaceutically acceptable salt thereof.

26. The minocycline compound of claim 1, wherein said compound is:

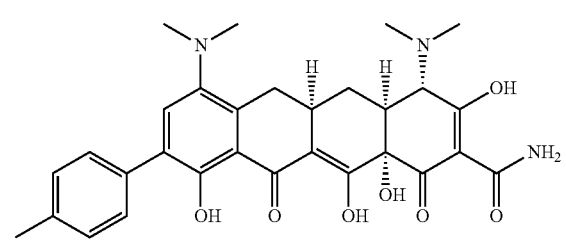

or a pharmaceutically acceptable salt thereof.

27. The minocycline compound of claim 1, wherein said compound is:

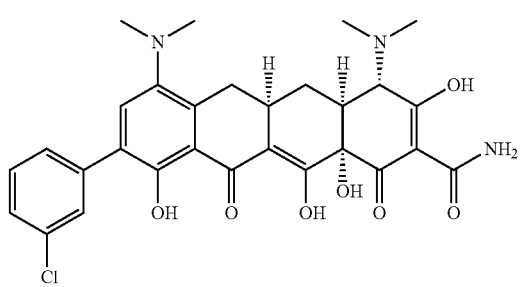

or a pharmaceutically acceptable salt thereof.

28. The minocycline compound of claim 1, wherein said compound is:

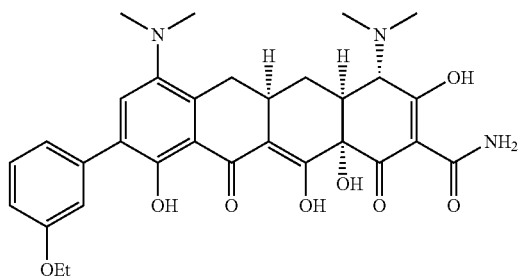

or a pharmaceutically acceptable salt thereof.

29. The minocycline compound of claim 1, wherein said compound is:

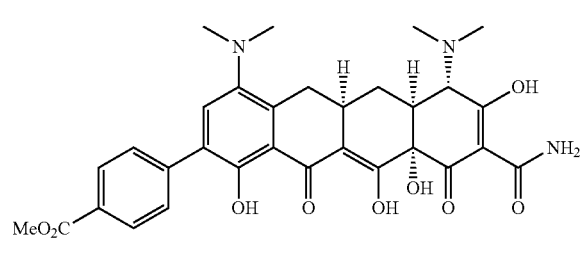

or a pharmaceutically acceptable salt thereof.

30. The minocycline compound of claim 1, wherein said compound is:

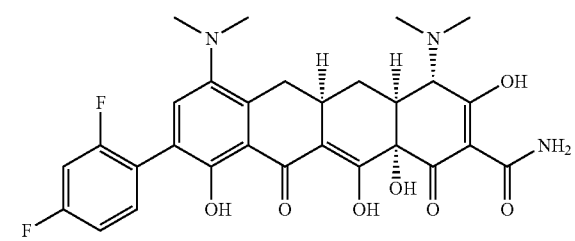

or a pharmaceutically acceptable salt thereof.

31. The minocycline compound of claim 1, wherein said compound is:

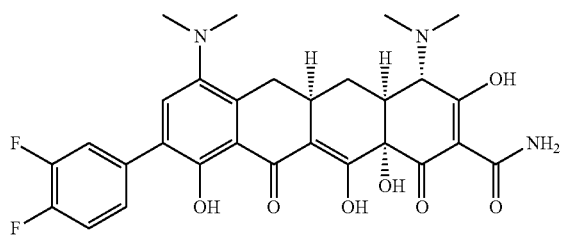

or a pharmaceutically acceptable salt thereof.

32. The minocycline compound of claim 1, wherein said compound is:

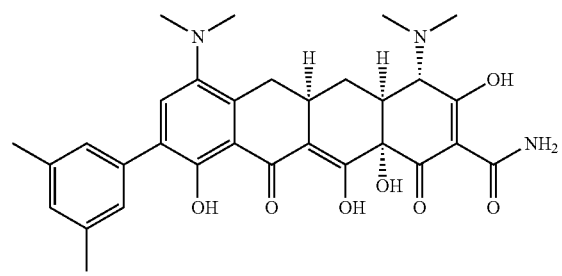

or a pharmaceutically acceptable salt thereof.

33. The minocycline compound of claim 1, wherein said compound is:

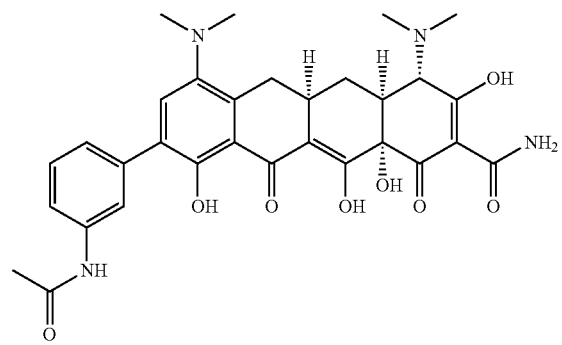

or a pharmaceutically acceptable salt thereof.

34. The minocycline compound of claim 1, wherein said compound is:

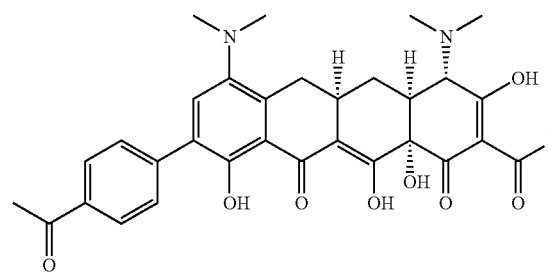

or a pharmaceutically acceptable salt thereof.

35. The minocycline compound of claim 1, wherein said compound is:

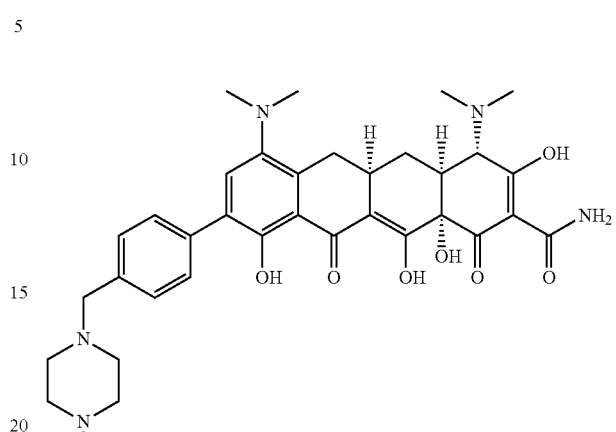

or a pharmaceutically acceptable salt thereof.

36. The minocycline compound of claim 1, wherein said compound is:

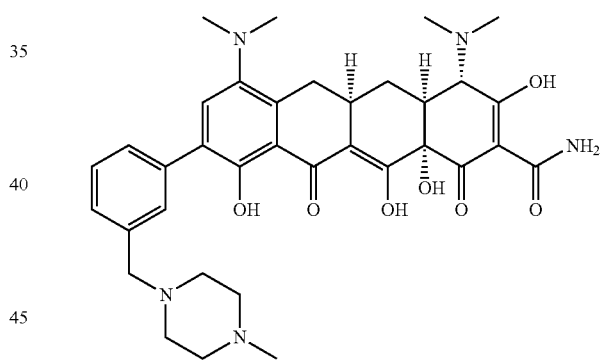

or a pharmaceutically acceptable salt thereof.

37. The minocycline compound of claim 1, wherein said compound is:

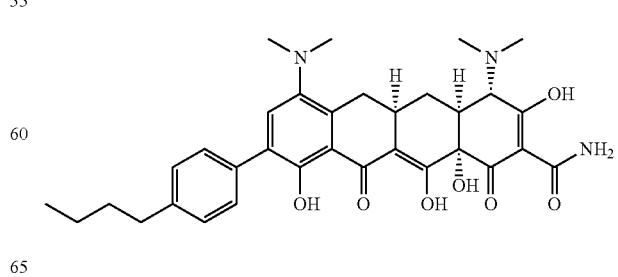

or a pharmaceutically acceptable salt thereof.

38. The minocycline compound of claim 1, wherein said compound is:

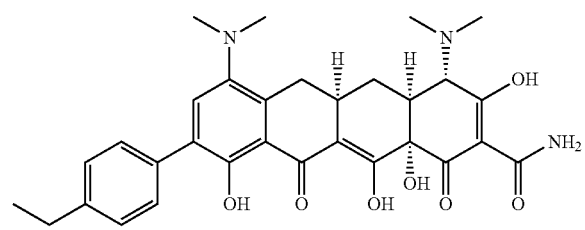

or a pharmaceutically acceptable salt thereof.

39. The minocycline compound of claim 1, wherein said compound is:

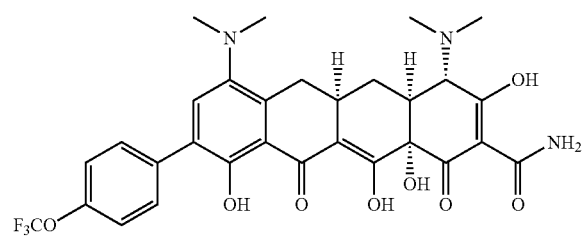

or a pharmaceutically acceptable salt thereof.

40. The minocycline compound of claim 1, wherein said compound is:

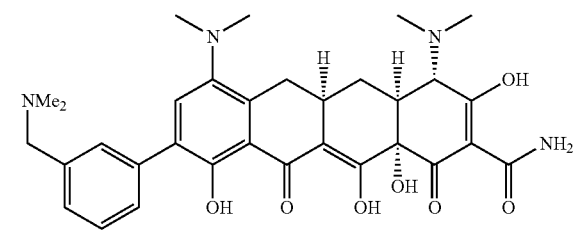

or a pharmaceutically acceptable salt thereof.

41. The minocycline compound of claim 1, wherein said compound is:

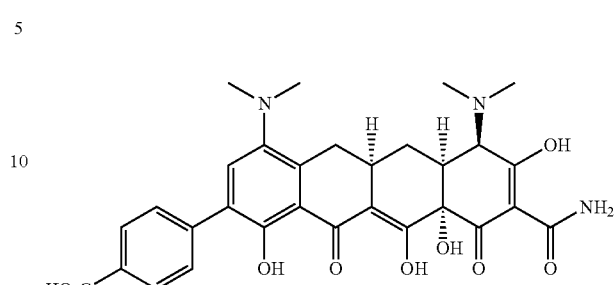

or a pharmaceutically acceptable salt thereof.

42. The minocycline compound of claim 1, wherein said compound is:

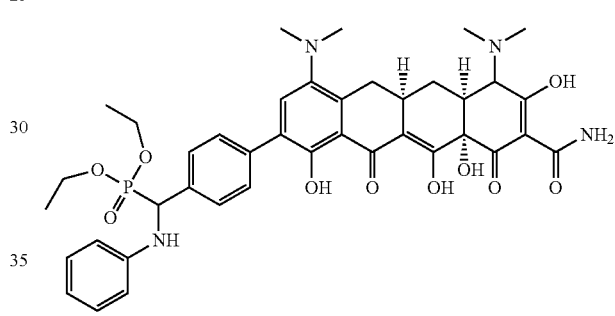

or a pharmaceutically acceptable salt thereof.

* * * * *